United States Patent
Wu et al.

(10) Patent No.: US 11,987,606 B2
(45) Date of Patent: *May 21, 2024

(54) COMPOSITIONS AND METHODS FOR ENHANCING AN IMMUNE RESPONSE

(71) Applicant: The Johns Hopkins University, Baltimore, MD (US)

(72) Inventors: Tzyy-Choou Wu, Stevenson, MD (US); Chih-Ping Mao, Baltimore, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 610 days.

This patent is subject to a terminal disclaimer.

(21) Appl. No.: 15/555,613

(22) PCT Filed: Mar. 4, 2016

(86) PCT No.: PCT/US2016/020874
§ 371 (c)(1),
(2) Date: Sep. 5, 2017

(87) PCT Pub. No.: WO2016/141284
PCT Pub. Date: Sep. 9, 2016

(65) Prior Publication Data
US 2018/0037621 A1     Feb. 8, 2018

Related U.S. Application Data

(60) Provisional application No. 62/128,327, filed on Mar. 4, 2015.

(51) Int. Cl.
| | |
|---|---|
| *A61K 39/00* | (2006.01) |
| *A61K 35/17* | (2015.01) |
| *A61K 39/385* | (2006.01) |
| *C07K 14/00* | (2006.01) |
| *C07K 14/47* | (2006.01) |
| *C07K 14/74* | (2006.01) |
| *C07K 14/77* | (2006.01) |
| *C12N 15/62* | (2006.01) |
| *A61K 35/12* | (2015.01) |

(52) U.S. Cl.
CPC .......... *C07K 14/4721* (2013.01); *A61K 35/17* (2013.01); *A61K 39/00* (2013.01); *A61K 39/0005* (2013.01); *A61K 39/385* (2013.01); *C07K 14/00* (2013.01); *C07K 14/47* (2013.01); *C07K 14/70539* (2013.01); *C07K 14/77* (2013.01); *C12N 15/62* (2013.01); *A61K 2035/124* (2013.01); *A61K 2039/57* (2013.01); *A61K 2039/6031* (2013.01); *A61K 2039/605* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 10,799,579 | B2 * | 10/2020 | Wu ................... | C07K 14/4721 |
| 2004/0022731 | A1 | 2/2004 | Bogdanov et al. | |
| 2006/0258584 | A1 * | 11/2006 | Lind ........................ | A61P 7/04 |
| | | | | 514/14.3 |
| 2013/0011394 | A1 * | 1/2013 | Knoetgen ........ | C07K 14/70539 |
| | | | | 424/133.1 |

OTHER PUBLICATIONS

HLA Nomenclature (2015) (Year: 2015).*
Liu et al (MHC Complex: Interaction with Peptides. IN: eLS. John Wiley & Sons, Ltd: Chichester, DOI: 10.1002/9780470015902. a0000922.pub2, 2011, pp. 1-12) (Year: 2011).*
Wieczorek et al (Front. Immunol. 2017, vol. 8, article 292: 1-16) (Year: 2017).*
Reche and Reinherz (G. Nicosia et al., Eds. ICARIS 2004, LNCS 3239: 189-1196) (Year: 2004).*
Celis et al (PNAS USA, 1994, 91: 2105-2109) (Year: 1994).*
Ochoa-Garay et al (Mol. Immunol. 1997, 34(3): 273-281) (Year: 1997).*
Ali-Khan et al (Curr. Prot. Prot. Sci. 2002, 22.1.1-22.1.19, Suppl. 30, John Wiley & Sons, Inc.) (Year: 2002).*
Woolhouse et al (Phil. Trans. R. Soc. B, 2012, 367: 2864-2871) (Year: 2012).*
Schumacher and Schreiber (Science, 2015, 348: 69-74) (Year: 2015).*
Buonaguro et al (Clin. Vacc. Immunol. 2011, 18(1): 23-34) (Year: 2011).*
Repana et al (Genome Biol. 2019 20: 1-12) (Year: 2019).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Marrack et al (Ann. Rev. Immunol. 2008, 26:171-203) (Year: 2008).*
Singh et al (J. Immunol. 2017, 199: 2203-2213) (Year: 2017).*
Mao et al (Canc. Res. Abstract 1342, AACR 106th Annual Meeting 2015, published 08/15) (Year: 2015).*

(Continued)

*Primary Examiner* — G. R. Ewoldt
*Assistant Examiner* — Marianne Dibrino
(74) *Attorney, Agent, or Firm* — Foley Hoag LLP; Hathaway P. Russell, Esq.

(57) ABSTRACT

The disclosure features compounds comprising an antigen portion, a soluble Major Histocompatibility Complex (MHC) molecule portion (e.g., all or an antigen-binding portion of a soluble MHC class I molecule), and a dynamic anchor portion (e.g., an agent, such as Annexin V, that binds to phosphatidylserine). The featured compounds are useful for a variety of therapeutic applications, including, e.g., enhancing a T cell response to an antigen of interest or enhancing a T cell-driven immune response by a subject to an antigen of interest (e.g., a cancer antigen or a microbial antigen).

13 Claims, 4 Drawing Sheets

Specification includes a Sequence Listing.

(56) References Cited

OTHER PUBLICATIONS

Yik et al (J. Immunol. 2002, 168: 3145-3149) (Year: 2002).*
Mottez et al (J. Exp. Med. 1995, 181: 493-502) (Year: 1995).*
Chen et al (Blood, 2005, 105: 3902-3909) (Year: 2005).*
Yao et al (Vaccine, 2013, 31: 2289-2294). (Year: 2013).*
UniProt Id. No. P30457 (2015) (Year: 2015).*
Luo et al (Tissue Antigens, 2002, 59: 370-380) (Year: 2002).*
UniProt Id. No. P61769 (2015) (Year: 2015).*
Kalos and June (Immunity, 2013, 39: 49-60, see entire reference (Year: 2013).*
Spranger, S (Int. Immunol. 2015, 28(8): 383-391) (Year: 2015).*
Beatty and Gladney (Clin. Canc. Res. 2014, 21(4): 687-692) (Year: 2014).*
Kerkar and Restifo (Cancer Res. 2012, 72(13): 3125-3130) (Year: 2012).*
McCulloch et al (Trends in Microbiol. 2022, 30: 158-169) (Year: 2022).*
International Search Report and Written Opinion for International Application No. PCT/US16/20874 dated Jun. 21, 2016.
Montaville et al., "A new consensus sequence for phosphatidylserine recognition by annexins," J Biol Chem, 277(27):24684-24693 (2002).
Ran et al., "Antitumor effects of a monoclonal antibody that binds anionic phospholipids on the surface of tumor blood vessels in mice," Clin Cancer Res, 11(4):1551-1562 (2005).

* cited by examiner

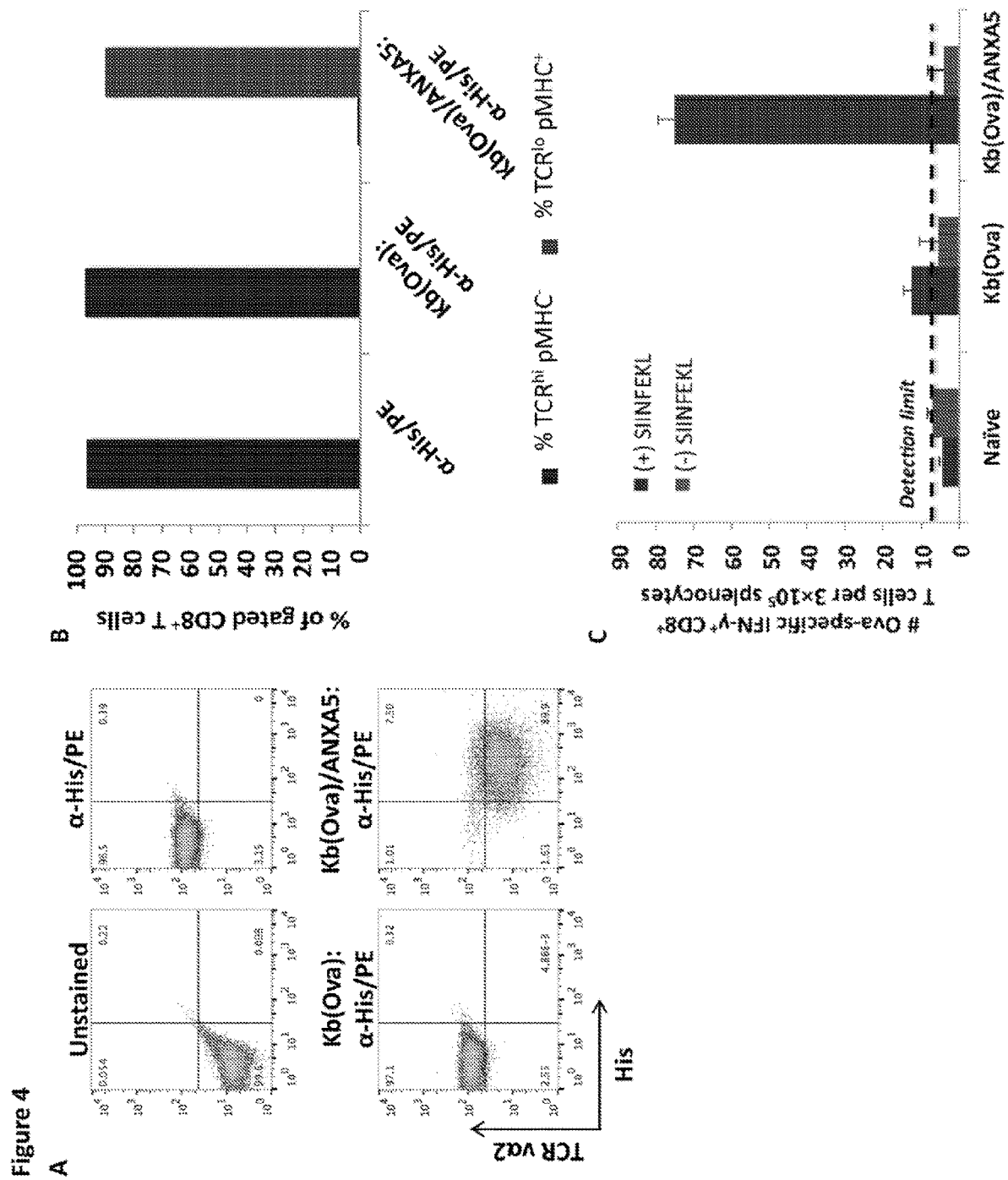

COMPOSITIONS AND METHODS FOR ENHANCING AN IMMUNE RESPONSE

CROSS REFERENCE TO RELATED APPLICATIONS

This application is a 371 National Stage Application of PCT/US16/020,874, filed Mar. 4, 2016, which claims priority to U.S. Provisional Application No. 62/128,327, filed Mar. 4, 2015, the contents of which are incorporated herein by reference in their entirety

GOVERNMENT SUPPORT

This invention was made with government support under grants CA114425 and CA194896 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Mar. 19, 2021, is named JHV-12901_SL.txt and is 33,089 bytes in size.

BACKGROUND

Due to their unique capacity to recognize a nearly infinite array of antigen variants with exquisite sensitivity, T cells have the potential to eradicate many types of diseases, such as microbial infections and cancer. In many instances, however, activation of a desired population of T cells by vaccination remains an elusive challenge. For example, in the case of cancer, although it has been shown that T cells can play a key role in the control of tumor progression, tumor-specific T cells almost universally suffer from a poor capacity to recognize tumor antigen due to intricate mechanisms of central and peripheral immune tolerance. See, e.g., Galon et al. (2006) *Science* 313:1960-1964; Zhang et al. (2003) *New Engl J Med* 348:203-213; Grivennikov et al. (2010) *Cell* 140:883-889; Laghi et al. (2009) *Lancet Oncol* 10:877-884; Swann and Smyth (2007) *J Clin Invest* 117: 1137-1146; Mueller (2010) *Nat Immunol* 11:21-27; and Starr et al. (2003) *Ann Rev Immunol* 21:139-176. Thus, there is a need in the art for improved methods for enhancing immune responses to diseases, such as cancer and infections.

SUMMARY

The disclosure is based, at least in part, on the development of compounds that produce and/or enhance T cell activation to an antigen of interest. The compounds comprise an antigen portion, a soluble Major Histocompatibility Complex (MHC) molecule portion (e.g., all or an antigen-binding portion of a soluble MHC class I molecule), and a dynamic anchor portion (e.g., an agent, such as Annexin V (also referred to herein as ANXA5), that binds to phosphatidylserine). While skilled artisans would recognize that the disclosure is not bound by any particular theory or mechanism of action, the compounds described herein utilize positive feedback-driven, programmed self-assembly of peptide-MHC (pMHC) directly on the membrane of T cells. Further, the compounds comprise a 'dynamic anchor' that senses and reacts to specific microenvironmental cues. The dynamic anchor—in a concerted and synergistic manner couples the early onset of TCR signaling by cognate pMHC with a surge in pMHC-TCR affinity, with repeated pMHC encounter, and with widespread TCR crosslinking. The dynamic anchor is linked to pMHC and firmly engages the plasma membrane of T cells upon the early onset of TCR signaling. This anchor, in turn, exerts a mechanical force that stabilizes interactions at the TCR-pMHC interface. Furthermore, once the dynamic anchor attaches to these T cells, it facilitates repeated, serial pMHC encounter, thereby prompting TCR crosslinking. As described below in the working examples, such compounds can augment activation of T cells by several orders of magnitude (>1,000-fold), as compared to use of the antigen alone. In addition, use of the compounds bypasses the need for costimulation, and can breaks tolerance against a model self-antigen in vivo.

Accordingly, in one aspect, the disclosure features a compound comprising: (a) a target antigen; (b) a soluble Major Histocompatibility Complex (MHC) molecule; and (c) a dynamic anchor, which binds to the surface of a T cell.

In some embodiments of any of the compositions described herein, the dynamic anchor is a phosphatidyl serine (PS)-binding agent, such as, e.g., an antibody (or an antigen-binding fragment thereof). The antibody can be, or comprise, a Fab fragment or an scFv fragment of an antibody.

In some embodiments, the dynamic anchor comprises, or is, an Annexin V molecule or a PS-binding portion thereof. For example, a consensus PS-binding site may comprise the sequence depicted in SEQ ID NO: 26 ([R/K]XXXK-BC-helices-[R/K]XXXXDXXS[D/E]+Ca2+) PubMed PMID: 11948176 (Montaville P, et al. A new consensus sequence for phosphatidylserine recognition by annexins. *J Biol Chem*. 2002 July 5; 277(27):24684-93). The Annexin V molecule comprises both the PS-binding domain and the self-assembly domain of Annexin V. Such a region may comprise five amino acid substitutions that abolish self-assembly in a combinatorial manner (R16E, R23E, K27E, K56E, K191E) PubMed PMID: 21468022(Bouter, A, et al. Annexin-A5 assembled into two-dimensional arrays promotes cell membrane repair. *Nat Commun*. 2011; 2:270). In some embodiments, the Annexin V molecule is a human Annexin V. In some embodiments, the Annexin V molecule comprises, or consists of, the amino acid sequence depicted in SEQ ID NO:1 or 2. In some embodiments, the Annexin V molecule comprises an amino acid sequence that is at least 80 (e.g., 81, 82, 83, 84, 85, 86, 87, 88, 89, 90, 91, 92, 93, 94, 95, 96, 97, 98, or 99%) identical to the amino acid sequence depicted in SEQ ID NO:1 or 2.

In some embodiments, the dynamic anchor is capable of self-assembly and/or facilitates self-assembly of two or more of the compounds on or at the T cell surface. Protein homodimerization domains, in addition to those of Annexin V, are well-known in the art.

In some embodiments of any of the compounds described herein, the antigen is or comprises a hapten. In some embodiments of any of the compounds described herein, the antigen is or comprises a peptide. In some embodiments of any of the compounds described herein, the antigen is a lipid or a sugar.

In some embodiments of any of the compounds described herein, the antigen is a microbial antigen. For example, the antigen can be a protein (or antigenic-portion thereof), a sugar (e.g., a polysaccharide), a lipid, a glycolipid, or a nucleic acid from a microbial source, e.g., a pathogenic microorganism. The microbe can be a virus, a bacterium, a fungus (e.g., yeast), or a protozoa.

In some embodiments of any of the methods described herein, the antigen comprises a viral protein, a bacterial protein, a fungal protein, a parasite protein, or an antigenic fragment of any of the foregoing. The viral protein can be a viral coat protein, e.g., an HIV-1 gag protein or an HIV-1 gp120 protein. In some embodiments, the parasite protein is a protozoan protein, such as CSP. In some embodiments, the antigen is a cancer antigen.

In some embodiments of any of the compounds described herein, the antigen is a tumor antigen.

In some embodiments, any of the compounds described herein comprise a calcium ion.

In some embodiments of any of the compounds described herein, the soluble MHC molecule is a HLA-A, HLA-B, HLA-C, DP, DO, or DR MHC molecule.

In some embodiments of any of the compounds described herein, the soluble MHC molecule is a soluble MHC class II molecule. The soluble MHC class II molecule can comprise, e.g., the α1 domain of a first MHC class II molecule and the β2 domain of a second MHC class II molecule. The first and second MHC class II molecule can be the same or different MHC class II molecules. In some embodiments, the soluble MHC class II molecule comprises the α2 domain of an MHC class II molecule. In some embodiments, the soluble MHC class II molecule comprises the β2 domain of an MHC class II molecule.

In some embodiments of any of the compounds described herein, the soluble MHC molecule is a soluble MHC class I molecule. The soluble MHC class I molecule can comprise, e.g., the α1 domain of an MHC class I molecule, the α2 domain of an MHC class I molecule, or both the α1 domain and the α2 domain of an MHC class I molecule. In some embodiments, the soluble MHC class I molecule comprises a 3-2 microglobulin polypeptide. In some embodiments, the soluble MHC class I molecule comprises the 03 domain of an MHC class I molecule.

In some embodiments of any of the compounds described herein, (a), (b), and (c) can be joined together by chemical conjugation. For example, in some embodiments, (b) and (c) are chemically conjugated.

In some embodiments, any of the compounds described herein can be, or comprise, a fusion protein. The fusion protein can comprise, e.g., (b) and (c). In some embodiments, the fusion protein can further comprise (a). In some embodiments, the fusion protein is arranged from amino-terminus to carboxy-terminus as (a), (b), and (c).

In some embodiments, any of the fusion proteins described herein can comprise at least one linker peptide. For example, at least one linker peptide can join (a) and (b). In some embodiments, at least one linker peptide can join (b) and (c). In some embodiments, (b) comprises a soluble MHC class I molecule and at least one linker peptide joins (a) to the α1 domain of an MHC class I molecule. In some embodiments, (b) comprises a soluble MHC class I molecule and at least one linker peptide joins (a) to the β-2 microglobulin polypeptide.

In some embodiments, any of the fusion proteins described herein can comprise the amino acid sequence depicted in SEQ ID NO:19:

(SEQ ID NO: 19)
MARSVTLVFLVLVSLTGLYASIINFEKLGGGASGGGGSGGGGSIQKTPQI

QVYSRHPPENGKPNILNCYVTQFHPPHIEIQMLKNGKKIPKVEMSDMSFS

KDWSFYILAHTEFTPTETDTYACRVKHASMAEPKTVYWDRDMGGGGSGGG

-continued
GSGGGGSGGGGSGPHSLRYFVTAVSRPGLGEPRYMEVGYVDDTEFVRFDS

DAENPRYEPQAPWMEQEGPEYWERETQKAKGNEQSFRVDLRTLLGYYNQS

KGGSHTIQVISGCEVGSDGRLLRGYQQYAYDGCDYIALNEDLKTWTAADM

AALITKHKWEQAGEAERLRAYLEGTCVEWLRRYLKNGNATLLRTDSPKAH

VTHHSRPEDKVTLRCWALGFYPADITLTWQLNGEELIQDMELVETRPAGD

GTFQKWASVVVPLGKEQYYTCHVYHQGLPEPLTLRWEPPPSTRSMAQVLR

GTVTDFPGFDERADAETLRKAMKGLGTDEESILTLLTSRSNAQRQEISAA

FKTLFGRDLLDDLKSELTGKFEKLIVALMKPSRLYDAYELKHALKGAGTN

EKVLTEIIASRTPEELRAIKQVYEEEYGSSLEDDVVGDTSGYYQRMLVVL

LQANRDPDAGIDEAQVEQDAQALFQAGELKWGTDEEKFITIFGTRSVSHL

RKVFDKYMTISGFQIEETIDRETSGNLEQLLLAVVKSIRSIPAYLAETLY

YAMKGAGTDDHTLIRVMVSRSEIDLFNIRKEFRKNFATSLYSMIKGDTSG

DYKKALLLLCGEDD.

SEQ ID NO: 19 contains a signal peptide of the mouse β2 microglobulin spanning amino acids 1-20 of SEQ ID NO: 19 (MARSVTLVFLVLVSLTGLYA, SEQ ID NO: 20), an ovalbumin epitope spanning amino acids 21-28 of SEQ ID NO: 19 (SIINFEKL, SEQ ID NO: 21), a linker spanning amino acids 29-43 of SEQ ID NO: 19 (GGGASGGGGSGGGGS, SEQ ID NO: 22), a β2 microglobulin without signal peptide spanning amino acids 44-142 of SEQ ID NO: 19 (IQKTPQIQVYSRHPPENGKPNILNCYVTQFHPPHIE-IQMLKNGKKIPKVEMSDMSFS KDWSFYILAHTEFTPTETDTYACRVKHASMAE-PKTVYWDRDM, SEQ ID NO: 23), a linker spanning amino acids 143-162 of SEQ ID NO: 19 (GGGGSGGGGSGGGGSGGGGS. SEQ ID NO: 15), a mouse MHC kb (without signal peptide and transmembrane) spanning amino acids 163-442 of SEQ ID NO: 19 (GPHSL-RYFVTAVSRPGLGEPRYMEVGYVDDTEFVRFDS-DAENPRYEPQAPWMEQ EGPEYWERETQKAKG-NEQSFRVDLRTLLGYYNQSKGGSHTIQVISGCEVGSD GRLL RGYQQYAYDGCDYIALNEDLKTWTAADMAA-LITKHKWEQAGEAERLRAYLEGT CVEWLR-RYLKNGNATLLRTD-SPKAHVTHHSRPEDKVTLRCWALGFYPADITLTW QLNGEELIQDMELVETRPAGDGTFQK-WASVVVPLGKEQYYTCHVYHQGLPEPLTL RWEPPPST, SEQ ID NO: 24), a linker spanning amino acids 443-444 of SEQ ID NO: 19 (RS, SEQ ID NO: 25), and the human annexin V (SEQ ID NO: 1) spanning amino acids 445-764 of SEQ ID NO: 19.

In some embodiments, the compounds described herein further comprise one or more cytokines (e.g., IL-2) or chemokines, which further enhance activation of a T cell or the subsequent T cell-driven immune response.

In another aspect, the disclosure features a nucleic acid comprising a nucleotide sequence encoding any one of the fusion proteins described herein. Also featured is a vector, e.g., an expression vector, comprising the nucleic acid.

In another aspect, the disclosure features a host cell comprising the vector or expression vector. The host cell can be eukaryotic (e.g., yeast, insect, mammalian, or plant) or prokaryotic. In some embodiments, the host cell is a rodent cell (CHO cell) or a non-human primate cell (COS cell). In some embodiments, the host cell is an NSO cell.

In another aspect, the disclosure features a method for producing a polypeptide. The method comprises culturing the host cell (above) under conditions suitable for expression of the precursor of the protein encoded by the nucleic acid to thereby produce the polypeptide. The method can further include isolating the polypeptide from the host cell or media in which the host cell was cultured. Also featured herein is a polypeptide produced using such a method.

In another aspect, the disclosure features a method for enhancing T cell activation. The method, which can be in vitro, ex vivo, or in vivo, comprises contacting a T cell specific for a target antigen with any one of the compounds described herein in an amount sufficient to enhance activation of the T cell.

In another aspect, the disclosure features a method (e.g., an in vitro, ex vivo, or in vivo method) for enhancing T cell activation, which method comprises contacting a plurality of immune cells comprising T cell specific for a target antigen with any of the compounds described herein in an amount sufficient to enhance T cell activation.

In some embodiments, the T cell or plurality of immune cells are obtained from a human. In some embodiments, the methods can also include obtaining the cells from a human (e.g., a blood draw). In some embodiments, the human has a cancer (e.g., a colon, brain, stomach, liver, pancreatic, skin, ocular, stomach, lung, esophageal, or hematologic cancer). In some embodiments, the human has an infection, e.g., by a pathogenic microorganism, such as a virus, a bacterium, a fungus, or a protozoan.

In some embodiments, any of the methods described herein can include, following the contacting, administering at least a portion of the plurality to the human. In some embodiments, any of the methods described herein can further comprise monitoring an immune response (e.g., the development or extent of an immune response) by the human to the target antigen.

In another aspect, the disclosure features a method for enhancing an immune response in a subject to a target antigen. The method comprises administering to the subject one or more of any of the compounds described herein in an amount effective to enhance an immune response to the target antigen. In some embodiments, the subject is a human, e.g., one having a cancer, a viral infection, a bacterial infection, a fungal infection, a protozoan infection.

In some embodiments, any of the methods described herein can further comprise monitoring an immune response (e.g., the development or extent of an immune response) by the human to the target antigen following administration of the compound.

"Polypeptide," "peptide," and "protein" are used interchangeably and mean any peptide-linked chain of amino acids, regardless of length or post-translational modification. As noted below, the polypeptides described herein can be, e.g., wild-type proteins, functional fragments of the wild-type proteins, or variants of the wild-type proteins or fragments. Variants, in accordance with the disclosure, can contain amino acid substitutions, deletions, or insertions. The substitutions can be conservative or non-conservative. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software. Appropriate parameters for measuring alignment, including any algorithms needed to achieve maximal alignment over the full-length of the sequences being compared can be determined by known methods.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for enhancing an immune response to an antigen in a mammal, will be apparent from the following description, the examples, and from the claims.

Figure 1:
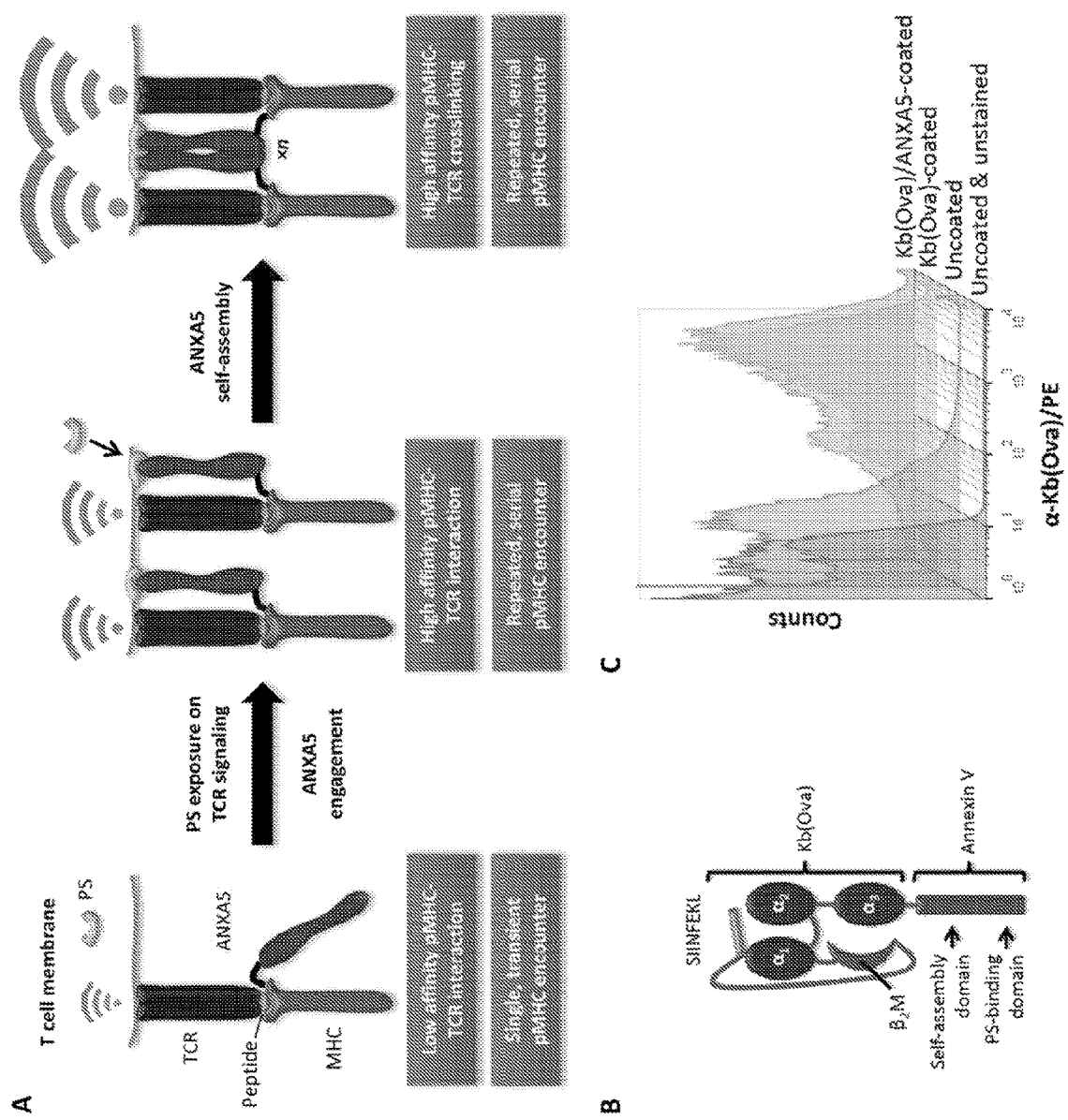
FIG. 1 depicts the design of a dynamic anchor-mediated programmed pMHC (peptide containing soluble MHC molecule) self-assembly, and consists of three panels: (A), (B), and (C). Panel (A) depicts a diagram of the dynamic anchor construct. Annexin V (ANXA5) functions as a dynamic anchor that does not interact with naïve T cells. Upon early onset of TCR signaling in cognate T cells, phosphatidylserine (PS) is presented on the outer leaflet of the plasma membrane. In turn, ANXA5 tightly engages the membrane, thereby fastening pMHC to the surface of T cells. This stabilizes interactions at the pMHC-TCR interface and enables repeated, serial pMHC encounters with the T cell receptor. ANXA5 also arranges into 2D matrices on the membrane, thereby facilitating TCR crosslinking. The outcome of this concerted sequence of events is the activation of low avidity T cells. Panel (B) depicts a schematic diagram of the pMHC containing ovalbumin epitope (SIINFEKL (SEQ ID NO: 21)), linker peptide, β2 microglobulin (β2M), and H-2Kb heavy chain linked to ANXA5. This construct is referred to as Kb(Ova)/ANXA5. Panel (C) depicts the results of an experiment in which liposomes coated with Kb(Ova)/ANXA5, Kb(Ova), or uncoated, were probed with phycoerythrin (PE)-labeled α-H-2Kb/SIINFEKL (SEQ ID NO: 21) mAb and assessed by flow cytometry.

Panel (A) depicts the results of experiments in which resting OT-I cells were pulsed with feeder cells loaded with SIINFEKL (SEQ ID NO: 21) peptide. Cells were stained with FITC-labeled ANXA5 and gated by FSC/SSC for flow cytometry analysis of PS exposure in T cells that underwent activation. Kinetics of PS exposure were quantified over time as the frequency of ANXA5+ cells (% binding) or FITC mean fluorescence intensity (binding intensity). Panel (B) depicts the results of experiments in which splenocytes from C57BL/6 mice were stimulated with plate-coated α-CD3 mAb overnight. Cells were then stained with FITC-labeled ANXA5, APC-labeled α-CD69 mAb, and PE-labeled α-CD8a mAb. Live CD8+ T cells were gated based on light scatter and CD8 expression, and CD69 expression and ANXA5 binding were assessed by flow cytometry. OT-I cells were incubated in the presence of Brefeldin A with pMHC (Kb(Ova)), ANXA5-linked pMHC (Kb(Ova)/ANXA5), or mutant Kb(Ova)/ANXA5 with disruptions (Panel (C)) in the calcium-binding domain (D144N, E228Q or D144N, E228Q, D303N) that abolish membrane binding or (Panel (D))) in the self-assembly domain (R16E, R23E, K27E, K56E, K191E). Activation of T cells after 12 hours was determined by flow cytometry analysis of IFN-7 expression.

FIG. 4 is a FACS scatter plot (Panel A) and a pair of bar graphs (Panels B and C) depicting ANXA5 acting as a membrane anchor of pMHC to overcome immune tolerance to self-antigen in vivo. Panel (A) shows the results of experiments in which His tag-bearing pMHC (Kb(Ova)) or ANXA5-linked pMHC (Kb(Ova)/ANXA5) was pre-mixed with PE-labeled α-His tag mAb and then incubated with resting OT-I cells at 37° C. for 5 hours. Cells were collected, stained for CD8 and TCR (Vα2), and examined for fluorescence by flow cytometry. Panel (B) depicts the percentage of cells classified into indicated categories of TCR surface density and pMHC binding was quantified. And Panel (C) depicts the results of an experiment in which transgenic 232-4 mice with ectopic expression of the ovalbumin (Ova) model antigen in the intestine were administered with either Kb(Ova) or Kb(Ova)/ANXA5 by subcutaneous injection. Splenocytes were collected and incubated overnight at 37° C. with Brefeldin A in the presence or absence of SIINFEKL (SEQ ID NO: 21) peptide. The frequency of IFN-γ+CD8+ T cells was determined by flow cytometry.

DETAILED DESCRIPTION

The present disclosure provides, among other things, compounds that promote, stimulate, induce, or enhance T cell activation to a target antigen. Also provided are applications, such as therapeutic and diagnostic methods, in which the compounds are useful. While in no way intended to be limiting, exemplary agents, compositions (e.g., pharmaceutical compositions and formulations), and methods for preparing and using these compounds and compositions are elaborated on below.

Compounds

The compounds described herein comprise: (a) a target antigen; (b) a soluble Major Histocompatibility Complex (MHC) molecule; and (c) dynamic anchor portion. An antigen is any substance that will induce a detectable (or measurable) immune response (e.g., humoral and/or cellular) when administered to a subject (e.g., a mammal, such as a human). For example, an antigen may be capable of inducing a measurable antibody response by the subject to which the antigen is administered. An effective amount of an antigen is one that is sufficient to activate an immune cell in culture and/or, in the in vivo setting, capable of inducing a measurable immune response by a mammal to the antigen. Representative antigens include peptides, proteins, polysaccharides, saccharides, lipids, nucleic acids, or combinations thereof. The antigen can be derived from a tumor or from a transformed cell such as a cancer or leukemic cell and can be a whole cell or immunogenic component thereof, e.g., cell wall components or molecular components thereof. In some embodiments, the antigen is a hapten.

Suitable antigens are known in the art and are available from commercial sources. The antigens may be purified or partially purified polypeptides derived from tumors or other sources. An antigen can have one or more epitopes, each of which being capable of inducing an immune response. In some embodiments, the antigen is derived from a microorganism. While in no way limiting, exemplary antigens can include proteins, carbohydrates, or lipids from any one of the following: viruses (e.g., HIV, rotavirus, influenza, parainfluenza, herpes (e.g., VZV, HSV-1, HAV-6, HSV-II, CMV, and Epstein Barr virus) Chicken pox, small pox, rabies, polio, Hepatitis A, Hepatitis B, Hepatitis C, measles, Dengue, mumps, Coxsackie virus, flaviviruses, adenoviruses, distemper, reovirus, respiratory syncytial virus, ebola, hanta virus, papillomavirus, and parvovirus), bacteria (e.g., *Bordetella pertussis, Brucella abortis, Escherichia coli, Salmonella* species, Streptococci, Cholera, *Shigella, Pseudomonas, Tuberculosis*, Pertussis, pneumonococci, meningococci, *Klebsiella proteus, legionella*, anthrax, leptospirosis), parasites (e.g., Plasmodiun, falciparun, *P. vivax, P. malariae, Entamoeba histolytica. Balantidium coli,* Naegleriatowleri, *Acanthamoeba* sp., *Giardia lambia,* Cryptosporidiiun sp., *Pneumocystis carinii, Plasmodium vivax, Babesia microti, Trypanosoma brucei, Trypanosoma cruzi, Leishmania donovani, Toxoplasma* gondi, and *JNippostrongylus brasiliensis*), or *Candida* (e.g., *albicans, krusei, glabrata,* or *tropicalis*), *Cryptococcus* neotornans, *Aspergillus* (e.g. fimigatus or *niger*), Mucorales (e.g., *mucor, absidia,* rhizophus), *Sporothrix schenkii,* Blasto.myces *dermatitidis, Paracoccidioides brasiliensis, Coccidioides irnmitis,* or *Histoplasma capsulatum*). Antigens also include Sporozoan antigens, *Plasmodium* antigens, such as all or a portion of Circumsporozoite protein, a Sporozoite surface protein, a liver stage antigen, an apical membrane associated protein, or a Merozoite surface protein. It is understood that a mammal described herein can, in some embodiments, be one infected with any of the foregoing microorganisms.

In some embodiments, the antigen is a tumor antigen, including (all or an antigenic portion of): alpha-actinin-4. Bcr-Abl, Casp-8, beta-catenin, cdc27, cdk4, cdkn2a, coa-1, dek-can, EF2, ETV6-AML1, LDLR-fucosyltransferaseAS, HLA-A2, HLA-All, hsp70-2, KIAAO205, Mart2, Mum-1, 2, and 3, neo-PAP, myosin class I, OS-9, pm1-RARα, PTPRK, K-ras, N-ras, Triosephosphate isomerase, Bage-1, Gage 3,4,5,6,7, GnTV, Herv-K-mel, Lage-1, Mage-A1,2,3, 4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, pI85erbB2, pI80erbB-3, c-met, nm-23H1, PSA, TAG-72-4, CA 19-9, CA 72-4, CAM 17,1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3

(CA 27,29BCAA), CA 195, CA 242, CA-50, CAM43, CD68KP1, CO-029, FGF-5, G250, Ga733 (EpCAM), HTgp-175, M344, MA-50, MG7-Ag, MOV18, NB70K, NY-CO-1, RCAS1, SDCCAG16, TA-90 (Mac-2 binding protein/cyclophilin C-associated protein), TAAL6, TAG72, TLP, and TPS.

In some embodiments, the antigen is one or more epitopes of a given antigen of interest. In some embodiments, the antigen is fewer than five (e.g., four, three, two, or one) epitopes of an antigen of interest. In some embodiments, the antigen portion is no greater than 30 (e.g., no greater than 29, 28, 27, 26, 25, 24, 23, 22, 21, 20, 19, 18, 17, 16, 15, 14, 13, 12, 11, 10, 9, 8, 7, 5, or 5) amino acids (or the equivalent molecular size in daltons). In some embodiments, the antigen portion is between 4 and 30, between 4 and 25, between 4 and 15, between 4 and 20, between 4 and 10, or between 4 and 8 amino acids in length.

In some embodiments, the antigen is or comprises an epitope that induces T cell activation. In some embodiments, the antigen is or comprises a peptide that is presented in the peptide-binding groove of a class I MHC complex and recognized by circulating memory or effector T-cells. Recognition of the peptide results in an immune response effecting the removal of the cell presenting such a peptide-class I MHC complex.

The "dynamic anchor" portion of the compound couples the early onset of TCR signaling induced by pMHC with a surge in pMHC-TCR affinity, with repeated pMHC encounter, and with widespread TCR crosslinking (FIG. 1, Panel A). To achieve this, the dynamic anchors described herein react to certain microenvironmental cues. In particular, the dynamic anchor (1) can recognize antigen-specific T cells in a positive feedback-driven process catalyzed by the onset of TCR signaling, (2) attach tightly to the membrane of these T cells, and (3) undergo rapid self-assembly upon binding to the membrane. One exemplary compound incorporates the protein Annexin V (ANXA5) as a dynamic anchor. ANXA5 has a high affinity for PS ($K_D$~$10^{-10}$ M) under physiologic calcium concentrations. ANXA5 is also characterized by a capacity to organize into uniform 2D matrices on the lipid bilayer.

In some embodiments, the dynamic anchor is an agent that binds to phosphatidyl serine (PS), i.e., a PS-binding agent. Such agents are well known in the art and include, e.g., Annexins (e.g., Annexin A1, A2, A4, and Annexin V, see below) and antibodies (including fragments thereof) that bind to PS. As used herein, the term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody. The term "antibody" also includes "antibody fragments," "antigen-binding fragments," or similar terminology, which refer to a fragment of an antibody that retains the ability to bind to PS. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) Structure 2(12):1121-1123; Rondon and Marasco (1997) Annual Review of Microbiology 5:257-283, the disclosures of each of which are incorporated herein by reference in their entirety. Bispecific antibodies (including DVD-Ig antibodies; see below) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) J Immunol Meth 2fL:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

Suitable methods for producing an antibody, or antigen-binding fragments thereof, in accordance with the disclosure are known in the art. Exemplary anti-PS antibodies are also known in the art and described in, e.g., International Patent Application No. WO 2001068709, Soares et al. (2008) *Nature Med* 14:1357-1362; U.S. Patent Application Publication No. 20140205544; and Igarashi et al. (1995) J Biochem 117(2):452-457.

In some embodiments, the PS-binding agent comprises Annexin V or a PS-binding fragment thereof. Annexin V can be, e.g., a human protein. The Annexin V protein can comprise or consist of the amino acid sequence depicted in SEQ ID NO:1 (full-length human Annexin V):

```
                    (SEQ ID NO: 1; UniProt Id. No. P08758)
MAQVLRGTVTDFPGFDERADAETLRKAMKGLGTDEESILTLLTSRSNAQ

RQEISAAFKTLFGRDLLDDLKSELTGKFEKLIVALMKPSRLYDAYELKH

ALKGAGTNEKVLTEIIASRTPEELRAIKQVYEEEYGSSLEDDVVGDTSG

YYQRMLVVLLQANRDPDAGIDEAQVEQDAQALFQAGELKWGTDEEKFIT

IFGTRSVSHLRKVFDKYMTISGFQIEETIDRETSGNLEQLLLAVVKSIR

SIPAYLAETLYYAMKGAGTDDHTLIRVMVSRSEIDLFNIRKEFRKNFAT

SLYSMIKGDTSGDYKKALLLLCGEDD;
``` or SEQ ID NO:2 (human Annexin V minus met 1):

```
                                    (SEQ ID NO: 2)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD.
```

In some embodiments, the protein can have an amino acid sequence that is at least 80 (e.g., at least 85, 90, 95, or 99) % identical to the amino acid sequence depicted in SEQ ID NO:1 or 2. In some embodiments, the protein can have the amino acid sequence depicted in SEQ ID NO:1 or 2 having no more than 30 (e.g., no more than 29, 28, 27, 26, 25, 24, 23.22, 21.20, 19, 18, 17, 16, 15, 14, 13, 12, 11, 10, 9, 8, 7, 6, 5, 4, 3, 2, or 1) amino acid substitutions, deletions, or insertions. The substitutions can be conservative, non-conservative, or a mixture of both.

As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, the Annexin V protein can comprise or consist of the amino acid sequence depicted in SEQ ID NO:3 (full-length murine Annexin V):

```
                    (SEQ ID NO: 3; UniProt Id. No. P48036)
MATRGTVTDFPGFDGRADAEVLRKAMKGLGTDEDSILNLLTSRSNAQRQ

EIAQEFKTLFGRDLVDDLKSELTGKFEKLIVAMMKPSRLYDAYELKHAL

KGAGTDEKVLTEIIASRTPEELSAIKQVYEEEYGSNLEDDVVGDTSGYY

QRMLVVLLQANRDPDTAIDDAQVELDAQALFQAGELKWGTDEEKFITIF

GTRSVSHLRRVFDKYMTISGFQIEETIDRETSGNLEQLLLAVVKSIRSI

PAYLAETLYYAMKGAGTDDHTLIRVVVSRSEIDLFNIRKEFRKNFATSL

YSMIKGDTSGDYKKALLLLCGGEDD;
``` or SEQ ID NO:4 (mouse Annexin V minus met 1):

```
                    (SEQ ID NO: 4)
ATRGTVTDFPGFDGRADAEVLRKAMKGLGTDEDSILNLLTSRSNAQRQEI

AQEFKTLFGRDLVDDLKSELTGKFEKLIVAMMKPSRLYDAYELKHALKGA

GTDEKVLTEIIASRTPEELSAIKQVYEEEYGSNLEDDVVGDTSGYYQRML

VVLLQANRDPDTAIDDAQVELDAQALFQAGELKWGTDEEKFITIFGTRSV

SHLRRVEDKYMTISGFQIEETIDRETSGNLEQLLLAVVKSIRSIPAYLAE

TLYYAMKGAGTDDHTLIRVVVSRSEIDLFNIRKEFRKNFATSLYSMIKGD

TSGDYKKALLLLCGGEDD.
```

Additional agents that bind to PS include, e.g., peptides described in Kapty et al. (2012) *J Biomol Screen* 17(10): 1293-12301; Shao et al. (2007) *Mol Imaging* 6(6:417-426; Thapa et al. (2008) *J Cell Mol Med* 12(5A):1649-1660; and Igarashi et al. (1995) *J Biol Chem* 270:29075-29078.

In some embodiments, the agent comprises a homodimerization domain. Such domains include, e.g., Fc constant regions of antibodies, RRM motifs (Sagnol et al. (2014) *Nucleic Acids Res* 42(15):10173), and motifs described in Gerber et al. (2004) *J Biol Chem* 279:21177-21182 Khadria et al. (2014) *JAm Chem Soc* 136(40):14068-14077 (describing Gly-zipper dimerization motifs); Iyer et al. (2007) *Mol Genet Metab* 92:151-159 (describing LXXLL and AF-2 domains); and Brosig and Langosch (1998) *Protein Sci* 7:1052-1056 (describing the glyophorin A protein dimerization motif).

In some embodiments of any of the compounds described herein, the soluble MHC molecule is a HLA-A, HLA-B, HLA-C, DP, DO, or DR MHC molecule. The sequences of exemplary MHC class I and class II molecules are known in the art and publicly accessible. For example, exemplary MHC class I alpha chains include, e.g., the sequences depicted in UniProt Id. Nos. P30511, P01891, P30493, and P13747). In some embodiments, the compound described herein comprises one or more of the α1, α2, and α3 domains of an HLA class I molecule. In some embodiments, the compound described herein comprises the α1 and α2 domains of an MHC class I molecule. In some embodiments, the compound described herein comprises the α1, α2, and α3 domains of an MHC class I molecule. One of skill in the art would easily recognize the domain structure of an MHC class I molecule. For example, within the exemplary HLA-G class I alpha chain having the following amino acid sequence:

```
                                  (SEQ ID NO: 17)
MVVMAPRTLFLLLSGALTLTETWAGSHSMRYFSAAVSRPGRGEPRFIAM

GYVDDTQFVRFDSDSACPRMEPRAPWVEQEGPEYWEEETRNTKAHAQTD

RMNLQTLRGYYNQSEASSHTLQWMIGCDLGSDGRLLRGYEQYAYDGKDY

LALNEDLRSWTAADTAAQISKRKCEAANVAEQRRAYLEGTCVEWLHRYL

ENGKEMLQRADPPKTHVTHHPVFDYEATLRCWALGFYPAEHLTWQRDGE

DQTQDVELVETRPAGDGTFQKWAAVVVPSGEEQRYTCHVQHEGLPEPLM

LRWKQSSLPTIPIMGIVAGLVVLAAVVTGAAVAAVLWRKKSSD,
```

α1 (underlined) includes amino acids 25-114; α2 (bolded) includes amino acids 115-206; and α3 (italicized) includes amino acids 207-298.

In another example, within the exemplary HLA-A class I alpha chain having the following amino acid sequence:

```
                                  (SEQ ID NO: 18; UniProt Id. No. P30457)
MAVMAPRTLVLLLSGALALTQTWAGSHSMRYFYTSVSRPGRGEPRFIAVG

YVDDTQFVRFDSDAASQRMEPRAPWIEQEGPEYWDRNTRNVKAQSQTDRV
```

-continued

DLGTLRGYYNQSEDGSHTIQRMYGCDVGPDGRFLRGYQQDAYDGKDYIAL

NEDLRSWTAADMAAQITQRKVVETAHEAEQWRAYLEGRCVEWLRRYLENG

KETLQRT*DAPKTHMTHHAVSDHEATLRCWALSFYPAEITLTWQRDGEDQT*

*QDTELVETRPAGDGTFQKWASVVVPSGQEQRYTCHVQHEGLPKPLTLRWE*

*PSSQPTIPIVGIIAGLVLFGAVIAGAVVAAVMWRRKSSDRKGGSYSQAAS*

*SDSAQGSDMSLTACKV,*

α1 (underlined) includes amino acids 25-114; α2 (bolded) includes amino acids 115-206; and α3 (italicized) includes amino acids 207-298.

It is understood that a soluble class I molecule can include, e.g., the α1 domain, the α1 and α2 domain, or the α1, α2, and α3 domains of an MHC class I molecule.

In some embodiments, the compound comprises a β2-microglobulin polypeptide, e.g., a human β2-microglobulin. In some embodiments, the B-2 microglobulin is wild-type human β-2 microglobulin. In some embodiments, the β-2 microglobulin comprises the following amino acid sequence: MSRSVALAVLALLSLSGLEAIQRTPKIQVYSRHPAE-NGKSNFLNCYVSGFH PSDIEV DLLKNGE-RIEKVEHSDLSFSKDWSFYLLYYTEFTPTEKDEY-ACRVNHVTLSQPKIV KWDRM (SEQ ID NO:5) (UniProt Id. No. P61769) or IQRTPKIQVYSRHPAENGKSNFLN-CYVSGFHPSDIEVDLLKNGERIEKVEHSDLSFSK DWSFYLLYYTEFTPTEKDEYACRVNHVTLSQP-KIVKWDRM (SEQ ID NO:6). In some embodiments, the s-2 microglobulin comprises an amino acid sequence that is at least 80, 85, 90, 95, or 99% identical to the amino acid sequence depicted in SEQ ID NO:5 or 6. In some embodiments, the β-2 microglobulin comprises the amino acid sequence of SEQ ID NO:5 or 6 having no more than 20 (e.g., no more than 19, 18, 17, 16, 15, 14, 13, 12, 11, 10, 9, 8, 7, 6, 5, 4, 3, 2, or 1) amino acid substitutions, deletions, or insertions.

In some embodiments, one or more of (a), (b), and (c) of the compounds described herein can be covalently linked together by chemical conjugation. Two proteins can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succin-imidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of a protein agent. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

In some embodiments, the compound can be a fusion protein comprising, e.g.: (a), (b), and (c); or (b) and (c). In some embodiments, the fusion protein is arranged from amino-terminus to carboxy-terminus as (a), (b), and (c).

In some embodiments, the compounds described herein can comprise one or more linker peptides (e.g., linking (a) to (b) and/or (b) to (c)). Exemplary linker peptides are known in the art and include, e.g., GS. GGS, GGGS (SEQ ID NO: 7). GGGSGGGS (SEQ ID NO: 8), GGGSGGGSGGGS (SEQ ID NO: 9), GGGSGGGSGGGSGGGS (SEQ ID NO: 10). GGGSGGGSGGGSGGGSGGGS (SEQ ID NO: 11). GGGGS (SEQ ID NO: 12), GGGGSGGGGS (SEQ ID NO: 13), GGGGSGGGGSGGGGS (SEQ ID NO: 14). GGGGSGGGGSGGGGSGGGGS (SEQ ID NO: 15), and GGGGSGGGGSGGGGSGGGGSGGGGS (SEQ ID NO: 16). Additional exemplary linker peptides are set forth herein, e.g., within the context of the fusion protein having the amino acid sequence depicted in SEQ ID NO:19.

The term "linker peptide" denotes amino acid sequences of natural and/or synthetic origin. They consist of a linear amino acid chain wherein the 20 naturally occurring amino acids are the monomeric building blocks. The peptide linker has a length of from 1 to 50 amino acids, in one embodiment between 1 and 28 amino acids, in a further embodiment between 2 and 25 amino acids. The peptide linker may contain repetitive amino acid sequences or sequences of naturally occurring polypeptides.

The linker has the function to ensure that polypeptides conjugated to each other can perform their biological activity by allowing the polypeptides to fold correctly and to be presented properly. In some embodiments, the peptide linker is rich in glycine, glutamine, and/or serine residues. These residues are arranged e.g. in small repetitive units of up to five amino acids. This small repetitive unit may be repeated for one to five times. At the amino and/or carboxy-terminal ends of the multimeric unit up to six additional arbitrary, naturally occurring amino acids may be added. Other synthetic peptidic linkers are composed of a single amino acid, which is repeated between 10 to 20 times and may comprise at the amino- and/or carboxy-terminal end up to six additional arbitrary, naturally occurring amino acids. All peptidic linkers can be encoded by a nucleic acid molecule and therefore can be recombinantly expressed. As the linkers are themselves peptides, the polypeptide connected by the linker are connected to the linker via a peptide bond that is formed between two amino acids.

In some embodiments, at least one linker peptide joins (a) and (b). In some embodiments, at least one linker peptide joins (b) and (c). In some embodiments, (b) comprises a soluble MHC class I molecule and at least one linker peptide joins (a) to the α1 domain of an MHC class I molecule. In some embodiments, (b) comprises a soluble MHC class I molecule and at least one linker peptide joins (a) to the β-2 microglobulin polypeptide. In some embodiments, (b) is a soluble MHC class I molecule and at least one linker peptide joins the β-2 microglobulin polypeptide to the α1 domain of an MHC class I alpha chain (See Panel A of FIG. 1).

In some embodiments, the compound comprises the amino acid sequence depicted in SEQ ID NO: 19. In some embodiments, the compound comprises an amino acid sequence that is at least 80 (e.g., at least 85, 90, 95, or 99)% identical to the amino acid sequence depicted in SEQ ID NO:19.

Expression Methods

A recombinant polypeptide (e.g., a fusion protein) can be produced using a variety of techniques known in the art of molecular biology and protein chemistry. For example, a nucleic acid encoding a fusion protein can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of recombinant polypeptides from nucleic acids in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA 76:2072) or Tn5 neo (Southern and Berg (1982) Mol Appl Genet 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147), cytomegalovirus, polyoma virus (Deans et al. (1984) Proc Natl Acad Sci USA 1:1292), or SV40 virus (Lusky and Botchan (1981) Nature 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of recombinant proteins include yeast, bacteria, insect, plant, and mammalian cells. Of particular interest are bacteria such as E. coli, fungi such as Saccharomyces cerevisiae and Pichia pastoris, insect cells such as SF9, mammalian cell lines (e.g., human cell lines), as well as primary cell lines.

In some embodiments, a recombinant protein can be expressed in, and purified from, transgenic animals (e.g., transgenic mammals). For example, a recombinant protein can be produced in transgenic non-human mammals (e.g., rodents) and isolated from milk as described in, e.g., Houdebine (2002) Curr Opin Biotechnol 13(6):625-629; van Kuik-Romeijn et al. (2000) Transgenic Res 9(2):155-159; and Pollock et al. (1999) J Immunol Methods 231(1-2):147-157.

A fusion protein can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, proteins expressed in E. coli can be refolded from inclusion bodies (see, e.g., Hou et al. (1998) Cytokine 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. A fusion protein described herein can be expressed in mammalian cells or in other expression systems including but not limited to yeast, baculovirus, and in vitro expression systems (see, e.g., Kaszubska et al. (2000) Protein Expression and Purification 18:213-220).

Following expression, the recombinant proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryotic or eukaryotic cell expressing the proteins. Typically, a polypeptide is purified when it constitutes at least 60 (e.g., at least 65, 70, 75, 80, 85, 90, 92, 95, 97, or 99) %, by weight, of the total protein in a sample.

The recombinant proteins can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, New York. The degree of purification necessary will vary depending on the desired use. In some instances, no purification of the expressed proteins will be necessary.

Methods for determining the yield or purity of a purified protein are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the protein preparations. Methods for removing endotoxin from a protein sample are known in the art and exemplified in the working examples. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), Mira- CLEAN® Endotoxin Removal Kit (Mirus), or Acrodisc™—Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated.

Pharmaceutical Compositions and Formulations

The compositions described herein can be formulated as a pharmaceutical solution, e.g., for administration to a subject for enhancing an immune response to an antigen. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

The compositions can be formulated according to standard methods. Pharmaceutical formulation is a well-established art, and is further described in, e.g., Gennaro (2000) "*Remington: The Science and Practice of Pharmacy,*" 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "*Handbook of Pharmaceutical Excipients* American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filtered sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 2:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions described herein are administered in an aqueous solution by parenteral injection. The disclosure features pharmaceutical compositions comprising an effective amount of the agent (or more than one agent) and optionally include pharmaceutically acceptable diluents, preservatives, solubilizers, emulsifiers, adjuvants and/or carriers. Such compositions include sterile water, buffered saline (e.g., Tris-HCl, acetate, phosphate). pH and ionic strength; and optionally, additives such as detergents and solubilizing agents (e.g., TWEEN® 20. TWEEN 80, Polysorbate 80), anti-oxidants (e.g., ascorbic acid, sodium metabisulfite), and preservatives (e.g., thimersol, benzyl alcohol) and bulking substances (e.g., lactose, mannitol). The formulations may be sterilized, e.g., using filtration, incorporating sterilizing agents into the compositions, by irradiating the compositions, or by heating the compositions.

As described above, relatively high concentration compositions can be made. For example, the compositions can be formulated at a concentration of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, Drugs and the Pharmaceutical Sciences, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

As used herein, "about" and like grammatical terms refers to an acceptable degree of error for the quantity measured given the nature or precision of the measurements. Exemplary degrees of error include up to 20% (e.g., no more than 19, 18, 17, 16, 15, 14, 12, 11, 10, 9, 8, 7, 6, 5, 4, 3, 2, 1, or less than 1%). In some embodiments, e.g., in biological systems, about includes values that are within an order of magnitude, e.g., within 4-fold, 3-fold, or 2-fold. In some embodiments, "about" refers to a value no more than 100% of the stated reference value.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) Science 20:1395-1398; Danos and Mulligan (1988) Proc Natl Acad Sci USA 8:6460-6464; Wilson et al. (1988) Proc Natl Acad Sci USA 8:3014-3018; Armentano et al. (1990) Proc. Natl. Acad. Sci. USA 7:6141-6145; Huber et al. (1991) Proc Natl Acad Sci USA 8:8039-8043; Ferry et al. (1991) Proc Natl Acad Sci USA 8:8377-8381; Chowdhury et al. (1991) Science 254:1802-1805; van Beusechem et al. (1992) Proc Natl Acad Sci USA 9:7640-7644; Kay et al. (1992) Human Gene Therapy 3:641-647; Dai et al. (1992) Proc Natl Acad Sci USA 9:10892-10895; Hwu et al. (1993) J Immunol 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) BioTechniques 6:616; Rosenfeld et al. (1991) Science 252:431-434; and Rosenfeld et al. (1992) Cell 8:143-155). Suitable adenoviral vectors derived from the adenovirus strain Ad type 5 d1324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) Am J Respir Cell Mol Biol 7:349-356; Samulski et al. (1989) J Virol 63:3822-3828; and McLaughlin et al. (1989) J Virol 62:1963-1973.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

Applications

The compounds described herein can be used in a number of in vitro, ex vivo, and in vivo applications. For example, the compounds described herein can be contacted to cultured cells in vitro or in vivo, or administered to a subject (e.g., a mammal, such as a human) to modulate the activation of an immune cell (e.g., a T cell) and/or modulate an immune response to an antigen of interest. For example, a T cell or a plurality of immune cells comprising T cells can be contacted with one or more of the compounds described herein in an amount effective to enhance activation of the immune cell by the antigen. The effective amount of the agent is the amount required to modulate the activation of the immune cell by the antigen, that is, to produce an enhanced or reduced activation level to the antigen as compared to the level of activation produced by the immune cell in the absence of the agent.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the immune cell is a T cell (e.g., a $CD8^+$ T cell, a CD3*CD8' T cell, a naïve T cell, or an NK cell). In some embodiments, the immune cell is a macrophage or a dendritic cell. Naïve T cells are mature T cells which have not yet encountered their cognate antigen within the periphery.

As used herein, the term "immune response" refers to the biological functions of immune cells (including macromolecules produced by such immune cells or the liver, such as antibodies, cytokines, and complement proteins) that result in selective damage to, destruction of, or elimination from the human body of invading pathogens, cells or tissues infected with pathogens, cancerous cells, or, in cases of autoimmunity or pathological inflammation, normal human cells or tissues. In some embodiments, the immune response is an innate immune response. In some embodiments, the immune response is a T cell response, e.g., a memory T cell response. In some embodiments, the immune response is a humoral immune response.

Immune cell activation (e.g., T cell activation) or like grammatical terms refers to one or more cellular responses of the subject immune cell, such as proliferation, maturation, differentiation, cytokine secretion, cytotoxic effector molecule release, cytotoxic activity, and expression of activation or differentiation markers. Suitable methods to measure activation of an immune cell (e.g., T cell activation, NK activation, or dendritic cell maturation) are known in the art and described in the working examples.

In some embodiments, the compound can be contacted to a plurality of immune cells, which plurality comprises T cells (e.g., CD8$^+$ T cells) and antigen presenting cells (and, optionally, B cells). For example, the plurality can be a population of splenocytes or peripheral blood mononuclear cells (PBMCs).

In some embodiments, the immune cell or plurality of immune cells is obtained from a mammal who has been exposed to the antigen or antigens of interest prior to the cells being obtained and, optionally, such prior exposure to the antigen resulted in the production of a measurable immune response to the antigen or antigens, e.g., the production of antibodies against the antigen or antigens. In some embodiments, the immune cell or plurality of cells is obtained from a patient known to be infected with a microbial pathogen (e.g., a virus, such as HIV-1). In some embodiments, the immune cell or plurality of immune cells is obtained from a patient with a cancer (e.g., a colon, brain, stomach, liver, pancreatic, skin, ocular, stomach, lung, esophageal, or hematologic cancer).

The above-described compounds are also useful to modulate (e.g., enhance) an immune response in a mammal. For example, an effective amount of compound can be administered to a mammal, wherein the immune response to the antigen portion of the compound by the mammal is enhanced in the presence of the compound. In some embodiments, the compound is administered in conjunction with one or more booster administrations of the antigen. In some embodiments, the compound is used ex vivo on a plurality of immune cells obtained from a patient. Following reintroduction of at least a portion of those immune cells contacted with the compound, the subject may receive one or more additional immunizations with the antigen of interest. In some embodiments, the subject is primed with an initial immunization against the antigen of interest prior to using the compound (containing all or part of the antigen) ex vivo or in vivo. In some embodiments, the compound and one or more boosts and/or priming immunizations are administered to the subject by different medical professionals. In some embodiments, the compound and one or more boosts and/or priming immunizations are administered to the subject by the same medical professional. In some embodiments, the compound and one or more boosts and/or priming immunizations are administered to the subject at different times (optionally by different routes of administration), but not more than 90 (e.g., not more than 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) day(s) apart.

In some embodiments, more than one dose of the compound is administered to the subject. In some embodiments, the compound and one or more boosts and/or priming immunizations are administered to the subject using different routes of administration. For example, the antigen can be administered subcutaneously or intramuscularly and the agent can be administered intravenously.

As used herein, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (e.g., enhanced T cell response to an antigen of interest, such as a cancer antigen).

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition. Preventing also includes reducing the likelihood of becoming productively infected by a microorganism against which the subject was immunized.

In some embodiments, the subject is one who has, is suspected of having, or is at risk for developing a cancer or an infection.

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer (i.e., a genetic predisposition to develop a cancer such as a mutation in a tumor suppressor gene (e.g., mutation in BRCA1, p53. RB, or APC) or has been exposed to conditions that can result in the condition. Thus, a subject can be one "at risk of developing a cancer when the subject has been exposed to mutagenic or carcinogenic levels of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus. Epstein-Barr virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., neuroblastoma), melanoma, thyroid cancer, ovarian cancer, testicular cancer, prostate cancer, cervical cancer, vaginal cancer, or bladder cancer. Hematological cancers (liquid tumors) include, e.g., leukemias (e.g., chronic lymphocytic leukemia such as B cell or T cell type chronic lymphocytic leukemia) and multiple myeloma. Bone cancers include, without limitation, osteosarcoma and osteocarcinomas.

Similarly, a subject at risk for developing at infection is one having one or more risk factors that increase the likelihood of exposure to a pathogenic microorganism.

A subject "suspected of having" a cancer or an infection is one having one or more symptoms of the cancer or infection. It should be understood that mammal at risk for developing, or suspected of having, a cancer or an infection does not include all mammals within the species of interest.

In some embodiments, the methods include determining whether the subject has a cancer or an infection.

In some embodiments, the subject is afflicted with a persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In addition, bacterial, fungal and other pathogenic infections are included, such as *Aspergillus, Brugia, Candida, Chlamydia, Coccidia, Cryptococcus, Dirofilaria, Gonococcus, Histoplasma, Leishmania, Mycobacterium, Mycoplasma,* Paramecium, Pertussis, *Plasmodium, Pneumococcus, Pneumocystis, Rickettsia, Salmonella, Shigella, Staphylococcus, Streptococcus, Toxoplasma* and Vibriocholerae. Exemplary species include *Neisseria* gonorrhea, *Mycobacterium tuberculosis, Candida albicans, Candida tropicalis, Trichomonas vaginalis, Haemophilus vaginalis,* Group B *Streptococcus* sp., Microplasma *hominis, Hemophilus ducreyi,* Granuloma inguinale, Lymphopathia venereum, *Treponema pallidum, Brucella abortus. Brucella melitensis, Brucella suis, Brucella canis, Campylobacter fetus, Campylobacter fetus intestinalis,* Leptospira pomona, *Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum.* Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L mexicana*) and *Plasmodium.*

The disclosure also features methods for enhancing an immune response in a subject afflicted with an infection (e.g., a viral, bacterial, or parasitic infection) or cancer (or in mammals at risk of developing a cancer or an infection, e.g., a viral infection, such as HIV-1, herpes, papillomavirus, or hepatitis infection) by administering to the mammal an effective amount of one or more of the compounds described herein.

In some embodiments, the subject is infected with HIV-1.

In some embodiments, the methods can include monitoring a subject (e.g., a human patient) for enhancement of an immune response to an antigen of interest. In some embodiments, for example, embodiments in which the mammal has an infection or a cancer, the methods can include evaluating the mammal for a change in a disease parameter, e.g., an improvement in one or more symptoms of a given disorder. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer or an infection.

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen. The precise dosage will vary according to a variety of factors such as subject-dependent variables (e.g., age, immune system health, etc.), the disease, and the treatment being effected. Therapeutically effective amounts of the agents disclosed herein enhance an immune response by a mammal to a target antigen.

Suitable human doses of any of the antibodies or fragments thereof described herein can further be evaluated in, e.g., Phase I dose escalation studies. See, e.g., van Gurp et al. (2008) *Am J Transplantation* &(U1:1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of cancer, vaccination, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LDs/ED_{50}$. Agents that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, an agent can be administered to a mammal in conjunction with one or more additional therapeutic agents (e.g., therapeutic agents for treating an infection (e.g., antivirals or antibiotics) or treating cancer).

Suitable additional anti-cancer therapies include, e.g., chemotherapeutic agents, ionizing radiation, immunotherapy agents, or hyperthermotherapy. Chemotherapeutic agents include, but are not limited to, aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, taxol, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF)-inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

The term "immunotherapeutic agent" can include any molecule, peptide, antibody or other agent which can stimulate a host immune system to generate an immune response to a tumor or cancer in the subject. Various immunotherapeutic agents are useful in the compositions are known in the art and include, e.g., PD-1 and/or PD-1L inhibitors, CD200 inhibitors, CTLA4 inhibitors, and the like. Exemplary PD-1/PD-L1 inhibitors (e.g., anti-PD-1 and/or anti-PD-L1 antibodies) are known in the art and described in, e.g., International Patent Application Publication Nos. WO 2010036959 and WO 2013/079174, as well as U.S. Pat. Nos. 8,552,154 and 7,521,051, the disclosures of each of which as they relate to the antibody descriptions are incorporated herein by reference in their entirety. Exemplary CD200 inhibitors are also known in the art and described in, e.g., International Patent Application Publication No. WO 2007084321. Suitable anti-CTLA4 antagonist agents are described in International Patent Application Publication Nos. WO 2001/014424 and WO 2004/035607; U.S. Patent Application Publication No. 2005/0201994; and European Patent No. EP 1212422. Additional CTLA-4 antibodies are described in U.S. Pat. Nos. 5,811,097, 5,855,887, 6,051,227, and 6,984,720. It is understood that the immunomodulatory agents can also be used in conjunction with a compound described herein for the treatment of an infection, such a viral, bacterial, or fungal infection, or any other condition in which an enhanced immune response to an antigen of interest would be therapeutically beneficial.

The following examples are intended to illustrate, not to limit, this disclosure.

EXAMPLES

Example 1. Generation and Characterization of Exemplary Compound

A compound was synthesized, which contained a recombinant single-chain pMHC (hereafter referred to as Kb(Ova)) composed of the H-2K$^b$-restricted ovalbumin (Ova) epitope (SIINFEKL (SEQ ID NO: 21)) linked to β2M and H-2K$^b$ heavy chain carrying deletions in the transmembrane domain and cytoplasmic tail. The α3 domain of H-2K$^b$ heavy chain in Kb(Ova) was connected to ANXA5 to create chimeric Kb(Ova)/ANXA5 (FIG. 1, Panel B). The binding of Kb(Ova)/ANXA5 to PS was confirmed by examining binding to immortalized cells treated by heat shock to provoke PS exposure. To evaluate the display of SIINFEKL (SEQ ID NO: 21) on H-2K$^b$ by the Kb(Ova) versus Kb(Ova)/ANXA5 proteins, His tag-carrying versions of these proteins were coated onto NTA:Ni$^+$ liposomes, probed with PE-labeled α-H-2K$^b$/Ova epitope mAb, and assessed PE fluorescence on liposomes by flow cytometry. Kb(Ova)- and Kb(Ova)/ANXA5-coated liposomes were both PE$^+$ (FIG. 1, Panel C). Importantly, Kb(Ova)-coated liposomes exhibited virtually identical fluorescence as Kb(Ova)/ANXA5-coated liposomes (FIG. 1, Panel C), indicating that the H-2K$^b$/Ova epitope complex is structurally intact on both the Kb(Ova) and Kb(Ova)/ANXA5 proteins and that fusion to ANXA5 does not alter the display of SIINFEKL (SEQ ID NO: 21) on H-2Kb.

Figure 2:
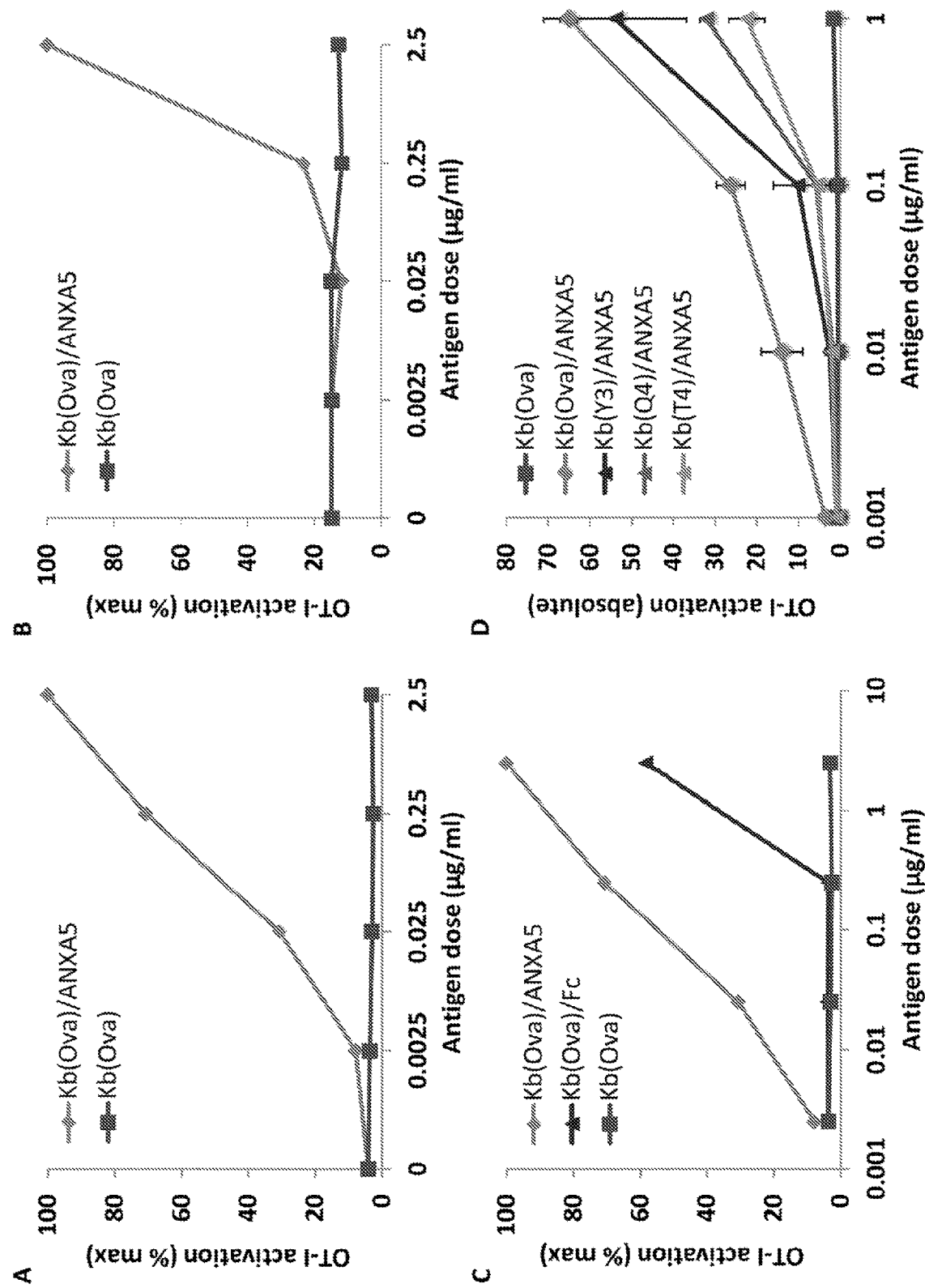
FIG. 2 is a series of line graphs represented in four panels: (A), (B), (C), and (D), which depict the activation of T cells by programmed pMHC self-assembly. Panel (A) depicts the results of the experiments using resting or (panel (B)) naïve OT-I cells were incubated with monomeric pMHC (Kb (Ova)) or ANXA5 anchor-linked pMHC (Kb(Ova)/ANXA5). OT-I cells were also incubated with dimeric pMHC (Kb(Ova)/Fc) (Panel (C)) or with ANXA5-linked APLs carrying indicated single amino acid substitutions in the SIINFEKL (SEQ ID NO: 21) epitope. Cells were incubated in the presence of Brefeldin A. Activation of T cells after 12 hours was determined by flow cytometry analysis of IFN-7 expression.

Example 2. Fusion of ANXA5 to pMHC Augments Activation of T Cells by Several Orders of Magnitude Resting (FIG. 2, Panel A) or naïve (FIG. 2, Panel B) Ova-specific CD8$^+$ T cells (OT-I) were incubated with Kb(Ova) or Kb(Ova)/ANXA5 at various doses in the presence of Brefeldin A (to block Golgi transport) and performed flow cytometry after 12 hour to detect IFN-7 expression as an index of activation. Kb(Ova)/ANXA5 was found to be greater than 1,000 times more potent than monomeric Kb(Ova) in activation of OT-I cells, as defined by the minimal dose of antigen required to detect activation (FIG. 2, Panels A and B). Kb(Ova)/ANXA5-but not Kb(Ova)- could induce robust activation of naïve Ova-specific T cells freshly isolated from OT-I transgenic mice without any costimulation (FIG. 2, Panel B). The activation of T cells by Kb(Ova)/ANXA5 versus dimeric Kb(Ova)/Fc was also compared; Kb(Ova)/ANXA5 was greater than 100 times more potent than Kb(Ova)/Fc (FIG. 2, Panel C). Kb(Ova)/ANXA5 did not elicit IFN-7 expression in non-cognate T cells even at high dose (>10 µg/ml), confirming that activation of T cells by Kb(Ova)/ANXA5 is antigen-specific. Furthermore, the viability, proliferation, and effector function of Ova-specific T cells pulsed with Kb(Ova)/ANXA5 was fully intact. To determine whether the compound could also stimulate T cells under a condition of low affinity TCR-pMHC interactions, a panel of Kb(Ova)/ANXA5 variants were synthesized, in which the variants contained altered peptide ligands (APLs) carrying critical single amino acid substitutions in the Ova epitope that markedly diminish the affinity for TCR (but not for H-2K$^b$). When linked to ANXA5, these APLs could induce robust activation of OT-I cells, far superior to the Kb(Ova) control carrying the wildtype SIINFEKL (SEQ ID NO: 21) epitope (FIG. 2, Panel D). Together, these data demonstrate that fusion of ANXA5 to pMHC augments activation of cognate T cells by several orders of magnitude and bypasses the need for costimulation, even when the pMHC-TCR interactions are weak.

Example 3. ANXA5 Selectively Binds to PS Externalized Following TCR Signaling

Figure 3:
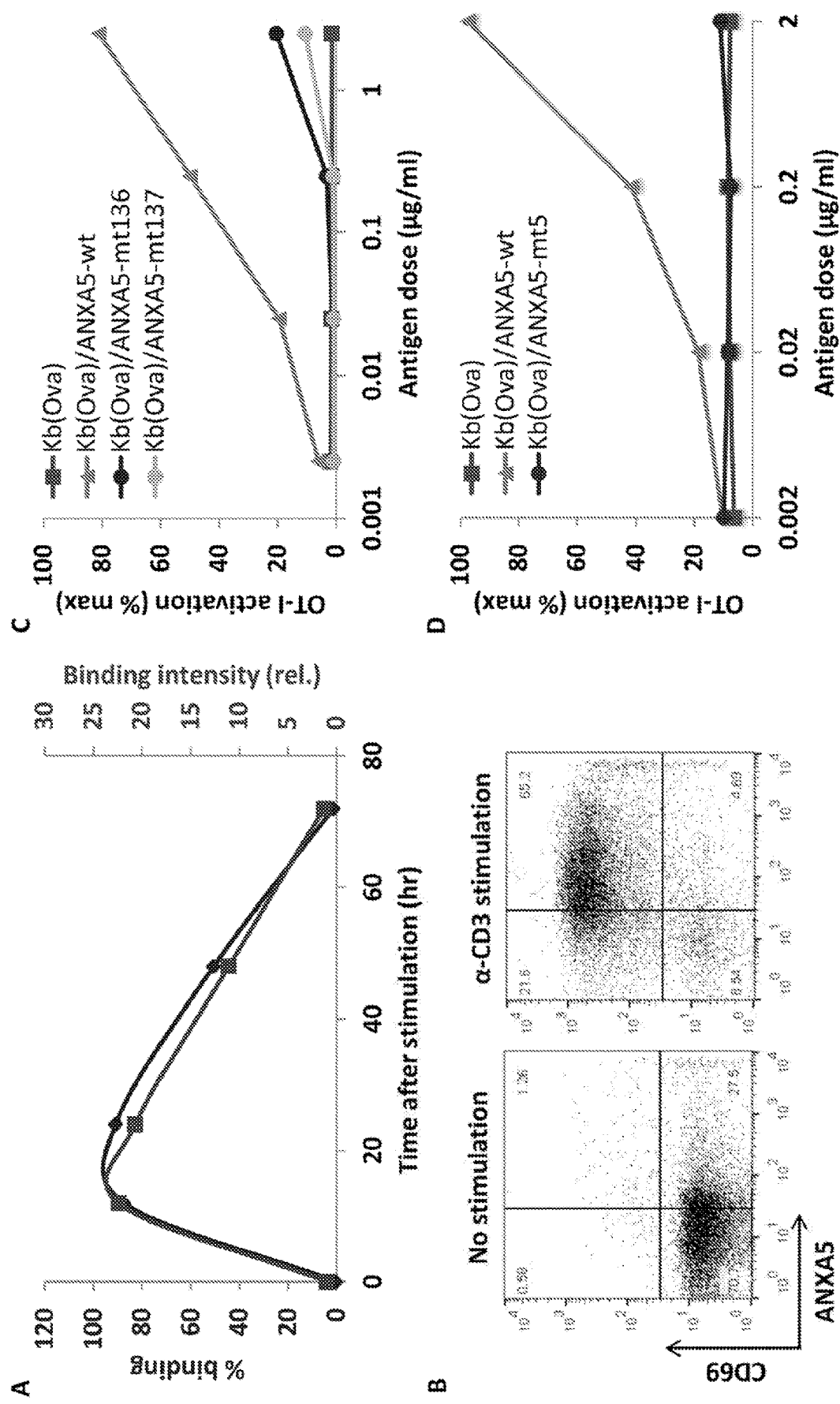
FIG. 3 is a series of line graphs (Panels A, C, and D) and a FACS scatter plot (Panel B) depicting the molecular mechanisms underlying programmed pMHC self-assembly.

To probe the molecular mechanisms underlying the effect of the dynamic anchor, OT-I cells were stimulated with SIINFEKL-loaded feeder cells and measured the binding kinetics of FITC-labeled ANXA5 to OT-I cells by flow cytometry at defined time points. OT-I cells externalized PS shortly after TCR signaling through pMHC, as nearly 100% of the cells attached strongly to ANXA5 (FIG. 3, Panel A). The kinetics of PS exposure on T cells were evaluated using flow cytometry; exposure was maximal at 12-24 hours after peptide stimulation and gradually decreased after that point (FIG. 3, Panel A); notably, these T cells were healthy and functional. These data demonstrate that PS is quickly and reversibly externalized by T cells upon TCR signaling through pMHC. To confirm ANXA5 binding to T cells on TCR signaling in a physiologic setting, splenocytes were isolated from C57BL/6 mice and incubated overnight at 37° C. with or without plate-coated with α-CD3 mAb. ANXA5 binding and activation (based on CD69 expression) of CD8-gated lymphocytes were evaluated by flow cytometry. The CD8$^+$ T cells in unstimulated splenocytes were almost all CD69$^-$ and had minimal binding to ANXA5 (FIG. 3, Panel B). By contrast, ~90% of CD8$^+$ T cells in α-CD3-stimulated splenocytes became CD69*(FIG. 3, Panel B). Furthermore, these CD69$^+$ CD8$^+$ T cells displayed prominent binding to ANXA5.

Example 4. Function of Self-Assembly Region

Based on the above data, it was believed that fusion of ANXA5 to pMHC would tether the pMHC to T cells upon TCR signaling in a positive feedback-driven process. Thus, chimeric pMHC/ANXA5 would exhibit both a high affinity and frequency of binding to cognate T cells. To test this, two mutant versions of Kb(Ova)/ANXA5 carrying amino acid substitutions in the calcium-binding domain of ANXA5 (D144N, E228Q or D144N, E228Q, D303N) which abolish interactions between ANXA5 and PS were synthesized. These mutant proteins could display intact SIINFEKL (SEQ ID NO: 21) peptide in the context of H-2K$^b$ (as in FIG. 1, Panel A) but failed to associate with PS. Activation of OT-I cells by mutant Kb(Ova)/ANXA5 proteins was severely impaired compared to wild-type Kb(Ova) (FIG. 3, Panel C), demonstrating that the ability of the dynamic anchor to attach to the membrane is critical for activation of cognate T cells. Also tested was the role of self-assembly in the immune-modulating function of ANXA5. To do so, a mutant Kb(Ova)/ANXA5 carrying 5 different amino acid substitutions (R16E, R23E, K27E, K56E, K191E) which prevent self-assembly of ANXA5 were tested. This mutant retains its ability to display Kb(Ova) and to associate with PS. Loss of self-assembly ability abrogated the capacity of this mutant Kb(Ova)/ANXA5 to stimulate OT-I cells (FIG. 3, Panel D).

Example 5. Fusion to ANXA5 Greatly Improves the Binding of pMHC to Cognate T Cells in an Antigen-Specific Manner To directly investigate the role of the dynamic anchor in fastening pMHC to the membrane, versions of Kb(Ova) or Kb(Ova)/ANXA5 carrying a His tag were pre-mixed with PE-labeled α-His mAb. The proteins were incubated with OT-I cells at 37° C. for 5 hours, stained for CD8 and TCR (Vα2 chain), and then pMHC binding and TCR expression were measured by flow cytometry. 98% of OT-I cells incubated with Kb(Ova)/ANXA5:α-His/PE complex became pMHC$^+$ (i.e. displayed PE fluorescence), with a mean fluorescence shift of 100-fold relative to the unstained control (FIG. 4, Panels A and B). By contrast, <1% of OT-I cells incubated with Kb(Ova):α-His/PE or with α-His/PE displayed PE fluorescence (FIG. 4, Panels A and B). Therefore, fusion to ANXA5 greatly improves the binding of pMHC to cognate T cells in an antigen-specific manner. Moreover, compared to the α-His/PE control, TCR Vα2 expression was downregulated by 90% of OT-I cells incubated with Kb(Ova)/ANXA5:α-His/PE but not by any of those cells incubated with Kb(Ova):α-His/PE (FIG. 4, Panel A and B). The TCR is downregulated in T cells as a consequence of TCR engagement by cognate pMHC. These data, support the conclusion that pMHC/ANXA5 acts on T cells to facilitate repeated, serial encounter with cognate TCR.

Example 6. The Exemplary Compound Overcomes Immune Tolerance to a Self Antigen

To test whether the dynamic anchor-driven programmed pMHC self-assembly may overcome immune tolerance to self-antigen in vivo, either Kb(Ova)/ANXA5 or Kb(Ova) was administered to transgenic mice (232-4) that exhibit ectopic expression of Ova in the intestine (Vezys et al. (2000) *Immunity* 12:505). In this model, Ova serves as a self antigen; therefore, endogenous CD8$^+$ T cells in 232-4 transgenic mice possess tolerance to Ova, and Ova-specific CD8$^+$ T cells cannot be elicited in these mice by conventional methods. A robust Ova-specific immune response was observed in 232-4 transgenic mice administered with Kb(Ova)/ANXA5 but not with Kb(Ova) (FIG. 4, Panel B). These data indicate that the exemplary compound is able to break immune tolerance to self-antigen.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A compound comprising: (a) a soluble Major Histocompatibility Complex (MHC) molecule; and (b) a dynamic anchor comprising Annexin V, wherein the MHC molecule comprises a class I MHC alpha chain comprising the amino acid sequence set forth in SEQ ID NO: 17 or SEQ ID NO: 18, and a β-2 microglobulin polypeptide comprising the sequence set forth in SEQ ID NO: 5 or SEQ ID NO: 6, and wherein the dynamic anchor comprises the amino acid sequence depicted in SEQ ID NO: 1 or 2.

2. The compound according to claim 1, wherein the dynamic anchor further comprises a homodimerization domain, or a calcium ion.

3. The compound according to claim 1, wherein the compound comprises a fusion protein arranged from amino terminus to carboxy-terminus as (a) and (b).

4. The compound according to claim 3, wherein the fusion protein comprises at least one linker peptide, wherein the at least one linker peptide comprises a linker peptide joining the MHC molecule of (a) and the dynamic anchor of (b).

5. The compound according to claim 4, wherein fusion protein comprises a second linker peptide joining the α1 domain of the MHC class I molecule alpha chain to the β-2 microglobulin polypeptide.

6. The compound according to claim 5, wherein the at least one linker peptide comprises one or more peptide sequences selected from: GS, GGS, and any of SEQ ID NOs: 7-16.

7. The compound according to claim 1, further comprising a peptide antigen, wherein the compound is made by a method comprising providing the MHC molecule in complex with the peptide antigen.

8. The compound according to claim 7, wherein the peptide antigen is covalently linked to the MHC molecule.

9. The compound according to claim 8, wherein a linker peptide joins the peptide antigen to either the class I MHC alpha chain or to the β-2 microglobulin polypeptide.

10. The compound according to claim 7, wherein the peptide antigen is a tumor-associated antigen.

11. The compound according to claim 7, wherein the peptide antigen is a microbial antigen.

12. A composition comprising the compound according to claim 7, and a pharmaceutically acceptable carrier.

13. The compound according to claim 10, wherein the tumor-associated antigen is a tumor-associated viral antigen selected from a human papillomavirus antigen, an Epstein-Barr virus antigen, a hepatitis B virus antigen, or a human T-cell leukemia-lymphoma virus antigen.

* * * * *

SEQUENCE LISTING

```
<160> NUMBER OF SEQ ID NOS: 26

<210> SEQ ID NO 1
<211> LENGTH: 320
<212> TYPE: PRT
<213> ORGANISM: Homo sapiens

<400> SEQUENCE: 1

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140
```

-continued

```
Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 2
<211> LENGTH: 319
<212> TYPE: PRT
<213> ORGANISM: Homo sapiens

<400> SEQUENCE: 2

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205
```

Phe Asp Lys Tyr Met Thr Ile Ser Gly Phe Gln Ile Glu Glu Thr Ile
            210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
290                 295                 300

Gly Asp Tyr Lys Lys Ala Leu Leu Leu Leu Cys Gly Glu Asp Asp
305                 310                 315

<210> SEQ ID NO 3
<211> LENGTH: 319
<212> TYPE: PRT
<213> ORGANISM: Homo sapiens

<400> SEQUENCE: 3

Met Ala Thr Arg Gly Thr Val Thr Asp Phe Pro Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ser Arg Ser Asn Ala Gln Arg
        35                  40                  45

Gln Glu Ile Ala Gln Glu Phe Lys Thr Leu Phe Gly Arg Asp Leu Val
    50                  55                  60

Asp Asp Leu Lys Ser Glu Leu Thr Gly Lys Phe Glu Lys Leu Ile Val
65                  70                  75                  80

Ala Met Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Ser Ala Ile Lys Gln Val Tyr Glu
        115                 120                 125

Glu Glu Tyr Gly Ser Asn Leu Glu Asp Asp Val Val Gly Asp Thr Ser
    130                 135                 140

Gly Tyr Tyr Gln Arg Met Leu Val Val Leu Leu Gln Ala Asn Arg Asp
145                 150                 155                 160

Pro Asp Thr Ala Ile Asp Asp Ala Gln Val Glu Leu Asp Ala Gln Ala
                165                 170                 175

Leu Phe Gln Ala Gly Glu Leu Lys Trp Gly Thr Asp Glu Glu Lys Phe
            180                 185                 190

Ile Thr Ile Phe Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
    210                 215                 220

Arg Glu Thr Ser Gly Asn Leu Glu Gln Leu Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Val Val

```
              260                 265                 270
Ser Arg Ser Glu Ile Asp Leu Phe Asn Ile Arg Lys Glu Phe Arg Lys
            275                 280                 285

Asn Phe Ala Thr Ser Leu Tyr Ser Met Ile Lys Gly Asp Thr Ser Gly
            290                 295                 300

Asp Tyr Lys Lys Ala Leu Leu Leu Cys Gly Gly Glu Asp Asp
305                 310                 315

<210> SEQ ID NO 4
<211> LENGTH: 318
<212> TYPE: PRT
<213> ORGANISM: Homo sapiens

<400> SEQUENCE: 4

Ala Thr Arg Gly Thr Val Thr Asp Phe Pro Gly Phe Asp Gly Arg Ala
1               5                   10                  15

Asp Ala Glu Val Leu Arg Lys Ala Met Lys Gly Leu Gly Thr Asp Glu
            20                  25                  30

Asp Ser Ile Leu Asn Leu Leu Thr Ser Arg Ser Asn Ala Gln Arg Gln
        35                  40                  45

Glu Ile Ala Gln Glu Phe Lys Thr Leu Phe Gly Arg Asp Leu Val Asp
50                  55                  60

Asp Leu Lys Ser Glu Leu Thr Gly Lys Phe Glu Lys Leu Ile Val Ala
65                  70                  75                  80

Met Met Lys Pro Ser Arg Leu Tyr Asp Ala Tyr Glu Leu Lys His Ala
                85                  90                  95

Leu Lys Gly Ala Gly Thr Asp Glu Lys Val Leu Thr Glu Ile Ile Ala
            100                 105                 110

Ser Arg Thr Pro Glu Glu Leu Ser Ala Ile Lys Gln Val Tyr Glu Glu
        115                 120                 125

Glu Tyr Gly Ser Asn Leu Glu Asp Asp Val Val Gly Asp Thr Ser Gly
130                 135                 140

Tyr Tyr Gln Arg Met Leu Val Val Leu Leu Gln Ala Asn Arg Asp Pro
145                 150                 155                 160

Asp Thr Ala Ile Asp Asp Ala Gln Val Glu Leu Asp Ala Gln Ala Leu
                165                 170                 175

Phe Gln Ala Gly Glu Leu Lys Trp Gly Thr Asp Glu Glu Lys Phe Ile
            180                 185                 190

Thr Ile Phe Gly Thr Arg Ser Val Ser His Leu Arg Arg Val Phe Asp
        195                 200                 205

Lys Tyr Met Thr Ile Ser Gly Phe Gln Ile Glu Glu Thr Ile Asp Arg
210                 215                 220

Glu Thr Ser Gly Asn Leu Glu Gln Leu Leu Leu Ala Val Val Lys Ser
225                 230                 235                 240

Ile Arg Ser Ile Pro Ala Tyr Leu Ala Glu Thr Leu Tyr Tyr Ala Met
                245                 250                 255

Lys Gly Ala Gly Thr Asp Asp His Thr Leu Ile Arg Val Val Val Ser
            260                 265                 270

Arg Ser Glu Ile Asp Leu Phe Asn Ile Arg Lys Glu Phe Arg Lys Asn
        275                 280                 285

Phe Ala Thr Ser Leu Tyr Ser Met Ile Lys Gly Asp Thr Ser Gly Asp
290                 295                 300

Tyr Lys Lys Ala Leu Leu Leu Cys Gly Gly Glu Asp Asp
305                 310                 315
```

<210> SEQ ID NO 5
<211> LENGTH: 118
<212> TYPE: PRT
<213> ORGANISM: Homo sapiens

<400> SEQUENCE: 5

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Met
        115

<210> SEQ ID NO 6
<211> LENGTH: 98
<212> TYPE: PRT
<213> ORGANISM: Homo sapiens

<400> SEQUENCE: 6

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Met

<210> SEQ ID NO 7
<211> LENGTH: 4
<212> TYPE: PRT
<213> ORGANISM: Artificial Sequence
<220> FEATURE:
<223> OTHER INFORMATION: linker

<400> SEQUENCE: 7

Gly Gly Gly Ser
1

<210> SEQ ID NO 8
<211> LENGTH: 8
<212> TYPE: PRT
<213> ORGANISM: Artificial Sequence
<220> FEATURE:

```
<223> OTHER INFORMATION: linker

<400> SEQUENCE: 8

Gly Gly Gly Ser Gly Gly Gly Ser
1               5

<210> SEQ ID NO 9
<211> LENGTH: 12
<212> TYPE: PRT
<213> ORGANISM: Artificial Sequence
<220> FEATURE:
<223> OTHER INFORMATION: linker

<400> SEQUENCE: 9

Gly Gly Gly Ser Gly Gly Gly Ser Gly Gly Gly Ser
1               5                   10

<210> SEQ ID NO 10
<211> LENGTH: 16
<212> TYPE: PRT
<213> ORGANISM: Artificial Sequence
<220> FEATURE:
<223> OTHER INFORMATION: linker

<400> SEQUENCE: 10

Gly Gly Gly Ser Gly Gly Gly Ser Gly Gly Gly Ser Gly Gly Gly Ser
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: linker

<400> SEQUENCE: 11

Gly Gly Gly Ser Gly Gly Gly Ser Gly Gly Gly Ser Gly Gly Gly Ser
1               5                   10                  15

Gly Gly Gly Ser
            20

<210> SEQ ID NO 12
<211> LENGTH: 5
<212> TYPE: PRT
<213> ORGANISM: Artificial Sequence
<220> FEATURE:
<223> OTHER INFORMATION: linker

<400> SEQUENCE: 12

Gly Gly Gly Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: linker

<400> SEQUENCE: 13

Gly Gly Gly Gly Ser Gly Gly Gly Gly Ser
1               5                   10

<210> SEQ ID NO 14
<211> LENGTH: 15
<212> TYPE: PRT
```

```
<213> ORGANISM: Artificial Sequence
<220> FEATURE:
<223> OTHER INFORMATION: linker

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: linker

<400> SEQUENCE: 15

Gly Gly Gly Gly Ser Gly Gly Gly Gly Ser Gly Gly Gly Gly Ser Gly
1               5                   10                  15

Gly Gly Gly Ser
            20

<210> SEQ ID NO 16
<211> LENGTH: 25
<212> TYPE: PRT
<213> ORGANISM: Artificial Sequence
<220> FEATURE:
<223> OTHER INFORMATION: linker

<400> SEQUENCE: 16

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 17
<211> LENGTH: 338
<212> TYPE: PRT
<213> ORGANISM: Homo sapiens

<400> SEQUENCE: 17

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160
```

```
Asp Thr Ala Ala Gln Ile Ser Lys Arg Lys Cys Glu Ala Ala Asn Val
            165                 170                 175

Ala Glu Gln Arg Arg Ala Tyr Leu Glu Gly Thr Cys Val Glu Trp Leu
        180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
        210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
            245                 250                 255

Thr Arg Pro Ala Gly Asp Gly Thr Phe Gln Lys Trp Ala Ala Val Val
        260                 265                 270

Val Pro Ser Gly Glu Glu Gln Arg Tyr Thr Cys His Val Gln His Glu
            275                 280                 285

Gly Leu Pro Glu Pro Leu Met Leu Arg Trp Lys Gln Ser Ser Leu Pro
        290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
            325                 330                 335

Ser Asp

<210> SEQ ID NO 18
<211> LENGTH: 365
<212> TYPE: PRT
<213> ORGANISM: Homo sapiens

<400> SEQUENCE: 18

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Arg Asn Thr Arg Asn Val Lys Ala Gln Ser Gln
            85                  90                  95

Thr Asp Arg Val Asp Leu Gly Thr Leu Arg Gly Tyr Tyr Asn Gln Ser
        100                 105                 110

Glu Asp Gly Ser His Thr Ile Gln Arg Met Tyr Gly Cys Asp Val Gly
    115                 120                 125

Pro Asp Gly Arg Phe Leu Arg Gly Tyr Gln Gln Asp Ala Tyr Asp Gly
        130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Thr Ala His Glu
            165                 170                 175

Ala Glu Gln Trp Arg Ala Tyr Leu Glu Gly Arg Cys Val Glu Trp Leu
        180                 185                 190
```

```
Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ser Val Val
                260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
        290                 295                 300

Thr Ile Pro Ile Val Gly Ile Ile Ala Gly Leu Val Leu Phe Gly Ala
305                 310                 315                 320

Val Ile Ala Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
                340                 345                 350

Ala Gln Gly Ser Asp Met Ser Leu Thr Ala Cys Lys Val
            355                 360                 365

<210> SEQ ID NO 19
<211> LENGTH: 764
<212> TYPE: PRT
<213> ORGANISM: Unknown
<220> FEATURE:
<223> OTHER INFORMATION: fusion

<400> SEQUENCE: 19

Met Ala Arg Ser Val Thr Leu Val Phe Leu Val Leu Val Ser Leu Thr
1               5                   10                  15

Gly Leu Tyr Ala Ser Ile Ile Asn Phe Glu Lys Leu Gly Gly Gly Ala
            20                  25                  30

Ser Gly Gly Gly Gly Ser Gly Gly Gly Ser Ile Gln Lys Thr Pro
        35                  40                  45

Gln Ile Gln Val Tyr Ser Arg His Pro Pro Glu Asn Gly Lys Pro Asn
    50                  55                  60

Ile Leu Asn Cys Tyr Val Thr Gln Phe His Pro Pro His Ile Glu Ile
65                  70                  75                  80

Gln Met Leu Lys Asn Gly Lys Lys Ile Pro Lys Val Glu Met Ser Asp
                85                  90                  95

Met Ser Phe Ser Lys Asp Trp Ser Phe Tyr Ile Leu Ala His Thr Glu
            100                 105                 110

Phe Thr Pro Thr Glu Thr Asp Thr Tyr Ala Cys Arg Val Lys His Ala
        115                 120                 125

Ser Met Ala Glu Pro Lys Thr Val Tyr Trp Asp Arg Asp Met Gly Gly
    130                 135                 140

Gly Gly Ser Gly Gly Gly Gly Ser Gly Gly Gly Gly Ser Gly Gly Gly
145                 150                 155                 160

Gly Ser Gly Pro His Ser Leu Arg Tyr Phe Val Thr Ala Val Ser Arg
                165                 170                 175

Pro Gly Leu Gly Glu Pro Arg Tyr Met Glu Val Gly Tyr Val Asp Asp
            180                 185                 190
```

```
Thr Glu Phe Val Arg Phe Asp Ser Asp Ala Glu Asn Pro Arg Tyr Glu
        195                 200                 205
Pro Gln Ala Pro Trp Met Glu Gln Gly Pro Glu Tyr Trp Glu Arg
210                 215                 220
Glu Thr Gln Lys Ala Lys Gly Asn Glu Gln Ser Phe Arg Val Asp Leu
225                 230                 235                 240
Arg Thr Leu Leu Gly Tyr Tyr Asn Gln Ser Lys Gly Gly Ser His Thr
                245                 250                 255
Ile Gln Val Ile Ser Gly Cys Glu Val Gly Ser Asp Gly Arg Leu Leu
            260                 265                 270
Arg Gly Tyr Gln Gln Tyr Ala Tyr Asp Gly Cys Asp Tyr Ile Ala Leu
        275                 280                 285
Asn Glu Asp Leu Lys Thr Trp Thr Ala Ala Asp Met Ala Ala Leu Ile
    290                 295                 300
Thr Lys His Lys Trp Glu Gln Ala Gly Glu Ala Glu Arg Leu Arg Ala
305                 310                 315                 320
Tyr Leu Glu Gly Thr Cys Val Glu Trp Leu Arg Arg Tyr Leu Lys Asn
                325                 330                 335
Gly Asn Ala Thr Leu Leu Arg Thr Asp Ser Pro Lys Ala His Val Thr
            340                 345                 350
His His Ser Arg Pro Glu Asp Lys Val Thr Leu Arg Cys Trp Ala Leu
        355                 360                 365
Gly Phe Tyr Pro Ala Asp Ile Thr Leu Thr Trp Gln Leu Asn Gly Glu
    370                 375                 380
Glu Leu Ile Gln Asp Met Glu Leu Val Glu Thr Arg Pro Ala Gly Asp
385                 390                 395                 400
Gly Thr Phe Gln Lys Trp Ala Ser Val Val Pro Leu Gly Lys Glu
                405                 410                 415
Gln Tyr Tyr Thr Cys His Val Tyr His Gln Gly Leu Pro Glu Pro Leu
            420                 425                 430
Thr Leu Arg Trp Glu Pro Pro Ser Thr Arg Ser Met Ala Gln Val
        435                 440                 445
Leu Arg Gly Thr Val Thr Asp Phe Pro Gly Phe Asp Glu Arg Ala Asp
450                 455                 460
Ala Glu Thr Leu Arg Lys Ala Met Lys Gly Leu Gly Thr Asp Glu Glu
465                 470                 475                 480
Ser Ile Leu Thr Leu Leu Thr Ser Arg Ser Asn Ala Gln Arg Gln Glu
                485                 490                 495
Ile Ser Ala Ala Phe Lys Thr Leu Phe Gly Arg Asp Leu Leu Asp Asp
            500                 505                 510
Leu Lys Ser Glu Leu Thr Gly Lys Phe Glu Lys Leu Ile Val Ala Leu
        515                 520                 525
Met Lys Pro Ser Arg Leu Tyr Asp Ala Tyr Glu Leu Lys His Ala Leu
    530                 535                 540
Lys Gly Ala Gly Thr Asn Glu Lys Val Leu Thr Glu Ile Ile Ala Ser
545                 550                 555                 560
Arg Thr Pro Glu Glu Leu Arg Ala Ile Lys Gln Val Tyr Glu Glu
                565                 570                 575
Tyr Gly Ser Ser Leu Glu Asp Asp Val Gly Asp Thr Ser Gly Tyr
            580                 585                 590
Tyr Gln Arg Met Leu Val Val Leu Leu Gln Ala Asn Arg Asp Pro Asp
        595                 600                 605
Ala Gly Ile Asp Glu Ala Gln Val Glu Gln Asp Ala Gln Ala Leu Phe
```

```
                610                 615                 620
Gln Ala Gly Glu Leu Lys Trp Gly Thr Asp Glu Glu Lys Phe Ile Thr
625                 630                 635                 640

Ile Phe Gly Thr Arg Ser Val Ser His Leu Arg Lys Val Phe Asp Lys
                645                 650                 655

Tyr Met Thr Ile Ser Gly Phe Gln Ile Glu Thr Ile Asp Arg Glu
            660                 665                 670

Thr Ser Gly Asn Leu Glu Gln Leu Leu Ala Val Val Lys Ser Ile
            675                 680                 685

Arg Ser Ile Pro Ala Tyr Leu Ala Glu Thr Leu Tyr Tyr Ala Met Lys
            690                 695                 700

Gly Ala Gly Thr Asp Asp His Thr Leu Ile Arg Val Met Val Ser Arg
705                 710                 715                 720

Ser Glu Ile Asp Leu Phe Asn Ile Arg Lys Glu Phe Arg Lys Asn Phe
                725                 730                 735

Ala Thr Ser Leu Tyr Ser Met Ile Lys Gly Asp Thr Ser Gly Asp Tyr
            740                 745                 750

Lys Lys Ala Leu Leu Leu Cys Gly Glu Asp Asp
            755                 760

<210> SEQ ID NO 20
<211> LENGTH: 20
<212> TYPE: PRT
<213> ORGANISM: Homo sapiens

<400> SEQUENCE: 20

Met Ala Arg Ser Val Thr Leu Val Phe Leu Val Leu Val Ser Leu Thr
1               5                   10                  15

Gly Leu Tyr Ala
            20

<210> SEQ ID NO 21
<211> LENGTH: 8
<212> TYPE: PRT
<213> ORGANISM: Homo sapiens

<400> SEQUENCE: 21

Ser Ile Ile Asn Phe Glu Lys Leu
1               5

<210> SEQ ID NO 22
<211> LENGTH: 15
<212> TYPE: PRT
<213> ORGANISM: Artificial Sequence
<220> FEATURE:
<223> OTHER INFORMATION: linker

<400> SEQUENCE: 22

Gly Gly Gly Ala Ser Gly Gly Gly Ser Gly Gly Gly Ser
1               5                   10                  15

<210> SEQ ID NO 23
<211> LENGTH: 99
<212> TYPE: PRT
<213> ORGANISM: Homo sapiens

<400> SEQUENCE: 23

Ile Gln Lys Thr Pro Gln Ile Gln Val Tyr Ser Arg His Pro Glu
1               5                   10                  15

Asn Gly Lys Pro Asn Ile Leu Asn Cys Tyr Val Thr Gln Phe His Pro
```

```
                 20                  25                  30
Pro His Ile Glu Ile Gln Met Leu Lys Asn Gly Lys Lys Ile Pro Lys
             35                  40                  45

Val Glu Met Ser Asp Met Ser Phe Ser Lys Asp Trp Ser Phe Tyr Ile
 50                  55                  60

Leu Ala His Thr Glu Phe Thr Pro Thr Glu Thr Asp Thr Tyr Ala Cys
 65                  70                  75                  80

Arg Val Lys His Ala Ser Met Ala Glu Pro Lys Thr Val Tyr Trp Asp
             85                  90                  95

Arg Asp Met

<210> SEQ ID NO 24
<211> LENGTH: 280
<212> TYPE: PRT
<213> ORGANISM: Mus musculus

<400> SEQUENCE: 24

Gly Pro His Ser Leu Arg Tyr Phe Val Thr Ala Val Ser Arg Pro Gly
 1               5                  10                  15

Leu Gly Glu Pro Arg Tyr Met Glu Val Gly Tyr Val Asp Asp Thr Glu
             20                  25                  30

Phe Val Arg Phe Asp Ser Asp Ala Glu Asn Pro Arg Tyr Glu Pro Gln
             35                  40                  45

Ala Pro Trp Met Glu Gln Glu Gly Pro Glu Tyr Trp Glu Arg Glu Thr
 50                  55                  60

Gln Lys Ala Lys Gly Asn Glu Gln Ser Phe Arg Val Asp Leu Arg Thr
 65                  70                  75                  80

Leu Leu Gly Tyr Tyr Asn Gln Ser Lys Gly Gly Ser His Thr Ile Gln
             85                  90                  95

Val Ile Ser Gly Cys Glu Val Gly Ser Asp Gly Arg Leu Leu Arg Gly
             100                 105                 110

Tyr Gln Gln Tyr Ala Tyr Asp Gly Cys Asp Tyr Ile Ala Leu Asn Glu
             115                 120                 125

Asp Leu Lys Thr Trp Thr Ala Ala Asp Met Ala Ala Leu Ile Thr Lys
 130                 135                 140

His Lys Trp Glu Gln Ala Gly Glu Ala Glu Arg Leu Arg Ala Tyr Leu
 145                 150                 155                 160

Glu Gly Thr Cys Val Glu Trp Leu Arg Arg Tyr Leu Lys Asn Gly Asn
             165                 170                 175

Ala Thr Leu Leu Arg Thr Asp Ser Pro Lys Ala His Val Thr His His
             180                 185                 190

Ser Arg Pro Glu Asp Lys Val Thr Leu Arg Cys Trp Ala Leu Gly Phe
             195                 200                 205

Tyr Pro Ala Asp Ile Thr Leu Thr Trp Gln Leu Asn Gly Glu Glu Leu
 210                 215                 220

Ile Gln Asp Met Glu Leu Val Glu Thr Arg Pro Ala Gly Asp Gly Thr
 225                 230                 235                 240

Phe Gln Lys Trp Ala Ser Val Val Val Pro Leu Gly Lys Glu Gln Tyr
             245                 250                 255

Tyr Thr Cys His Val Tyr His Gln Gly Leu Pro Glu Pro Leu Thr Leu
             260                 265                 270

Arg Trp Glu Pro Pro Ser Thr
 275                 280
```

```
<210> SEQ ID NO 25
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser
1

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(4)
<223> OTHER INFORMATION: Any amino acid
<220> FEATURE:
<221> NAME/KEY: NON_CONS
<222> LOCATION: (5)..(6)
<223> OTHER INFORMATION: Residues at these positions are separated by
      BC-helix sequences
<220> FEATURE:
<221> NAME/KEY: MOD_RES
<222> LOCATION: (6)..(6)
<223> OTHER INFORMATION: Arg or Lys
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(15)
<223> OTHER INFORMATION: Asp or Glu

<400> SEQUENCE: 26

Xaa Xaa Xaa Xaa Lys Xaa Xaa Xaa Xaa Xaa Asp Xaa Xaa Ser Xaa
1               5                   10                  15
```